United States Patent
Kohl et al.

(10) Patent No.: US 7,601,737 B2
(45) Date of Patent: Oct. 13, 2009

(54) ISOTOPICALLY SUBSTITUTED PROTON PUMP INHIBITORS

(75) Inventors: Bernhard Kohl, Constance (DE); Bernd Müller, Constance (DE); Dieter Haag, Lausen (DE); Wolfgang-Alexander Simon, Constance (DE); Karl Zech, Constance (DE); Michael David, Stockach (DE); Oliver Von Richter, Constance (DE); Felix Huth, Constance (DE)

(73) Assignee: Nycomed GmbH, Constance (DE)

( * ) Notice: Subject to any disclaimer, the term of this patent is extended or adjusted under 35 U.S.C. 154(b) by 0 days.

(21) Appl. No.: 12/000,376

(22) Filed: Dec. 12, 2007

(65) Prior Publication Data

US 2008/0146610 A1 Jun. 19, 2008

Related U.S. Application Data

(63) Continuation of application No. PCT/EP2006/064669, filed on Jul. 26, 2006, and a continuation of application No. PCT/EP2006/064666, filed on Jul. 26, 2006.

(30) Foreign Application Priority Data

| Jul. 26, 2005 | (EP) | ................................. | 05106868 |
| Jul. 26, 2005 | (EP) | ................................. | 05106874 |

(51) Int. Cl.
*A61K 31/437* (2006.01)
*C07D 471/04* (2006.01)

(52) U.S. Cl. ...................... 514/303; 546/118

(58) Field of Classification Search ............. 546/273.7, 546/118; 514/338, 303
See application file for complete search history.

(56) References Cited

U.S. PATENT DOCUMENTS

| 4,758,579 | A | 7/1988 | Kohl et al. |
| 6,818,200 | B2 | 11/2004 | Foster et al. |
| 6,872,408 | B2 | 3/2005 | Bell |
| 6,881,734 | B2 | 4/2005 | O'Neill et al. |
| 7,317,039 | B2 | 1/2008 | Alken |
| 2007/0082929 | A1* | 4/2007 | Gant et al. ................. 514/338 |

FOREIGN PATENT DOCUMENTS

| DE | 44 27 690 A1 | 2/1996 |
| EP | 0 005 129 B1 | 10/1979 |
| EP | 0 166 287 A1 | 1/1986 |
| EP | 0 174 726 A1 | 3/1986 |
| EP | 0 254 588 A1 | 1/1988 |
| EP | 0 268 956 A2 | 6/1988 |
| ES | 2 036 948 B1 | 6/1993 |
| WO | 92/08716 A1 | 5/1992 |
| WO | 03/050101 A1 | 6/2003 |
| WO | 2004/052881 A2 | 6/2004 |
| WO | 2007/041630 A1 | 4/2007 |

OTHER PUBLICATIONS

Vippagunta et al., "Crystalline Soilid", Advanced Drug Delivery Reviews 48 (2001) 3-26.*
Guillory in Brittain ed., "Polymorphism, etc.," NY: Marcel Dekker, Inc., 1999, 1-2, 183-226.*
Stenhoff, H., et al., "Determination of the enantiomers of omeprazole in blood plasma by normal-phase liquid chromatography and detection by atmospheric pressure ionization tandem mass spectrometry", Journal of Chromatography B, vol. 734, pp. 191-201, (1999).
Tolonen, A., et al., "A simple method for differentiation of monoisotopic drug metabolites with hydrogen-deuterium exchange liquid chromatography/electrospray mass spectrometry", European Journal of Pharmaceutical Sciences, vol. 25, pp. 155-162, (2005).
Helander, H.F., et al., "Localization of omeprazole and metabolites in the mouse", Scand J Gastroentrol, vol. 20, Suppl. 108, pp. 95-104, (1985).
Sjöström, J.E., et al., "In Vitro Antibacterial Activity of Omeprazole and Its Selectivity for Helicobacter spp. Are Dependent on Incubation Conditions", Antimicrobial Agents and Chemotherapy, vol. 40, No. 3, pp. 621-626, (1996).
Tanaka, M., et al., "Differential Stereoselective Pharmacokinetics of Pantoprazole, a Proton Pump Inhibitor in Extensive and Poor Metabolizers of Pantoprazole—A Preliminary Study", Chirality, vol. 9, pp. 17-21, (1997).
Hoffmann, K-J., "Identification of the Main Urinary Metabolites of Omeprazole after an Oral Dose to Rats and Dogs", Drug Metabolism and Disposition, vol. 14, No. 3, pp. 341-348, (1986).
Helander, H.F., et al., "Localization of omeprazole in the mouse", Gastroenterology, vol. 86, p. 1109, (1984).
Brändström, A., et al., "Chemical Reactions of Omeprazole and Omeprazole Analogues. III. Protolytic Behaviour of Compounds in the Omeprazole System", Acta Chemica Scandinavica, vol. 43, pp. 569-576, (1989).

* cited by examiner

*Primary Examiner*—Patricia L Morris
(74) *Attorney, Agent, or Firm*—The Nath Law Group; Joshua B. Goldberg; Sheldon M. McGee

(57) ABSTRACT

The invention relates to compounds of formula 1

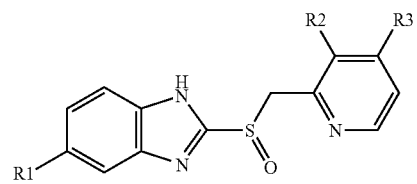

and formula 10

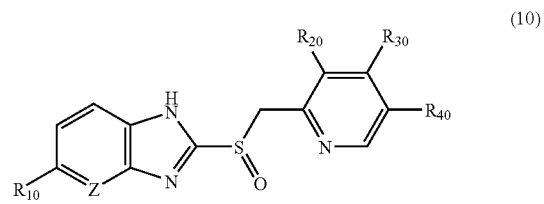

and to compositions comprising these compounds and methods of treating gastrointestinal disorders by administering these compounds.

21 Claims, 7 Drawing Sheets

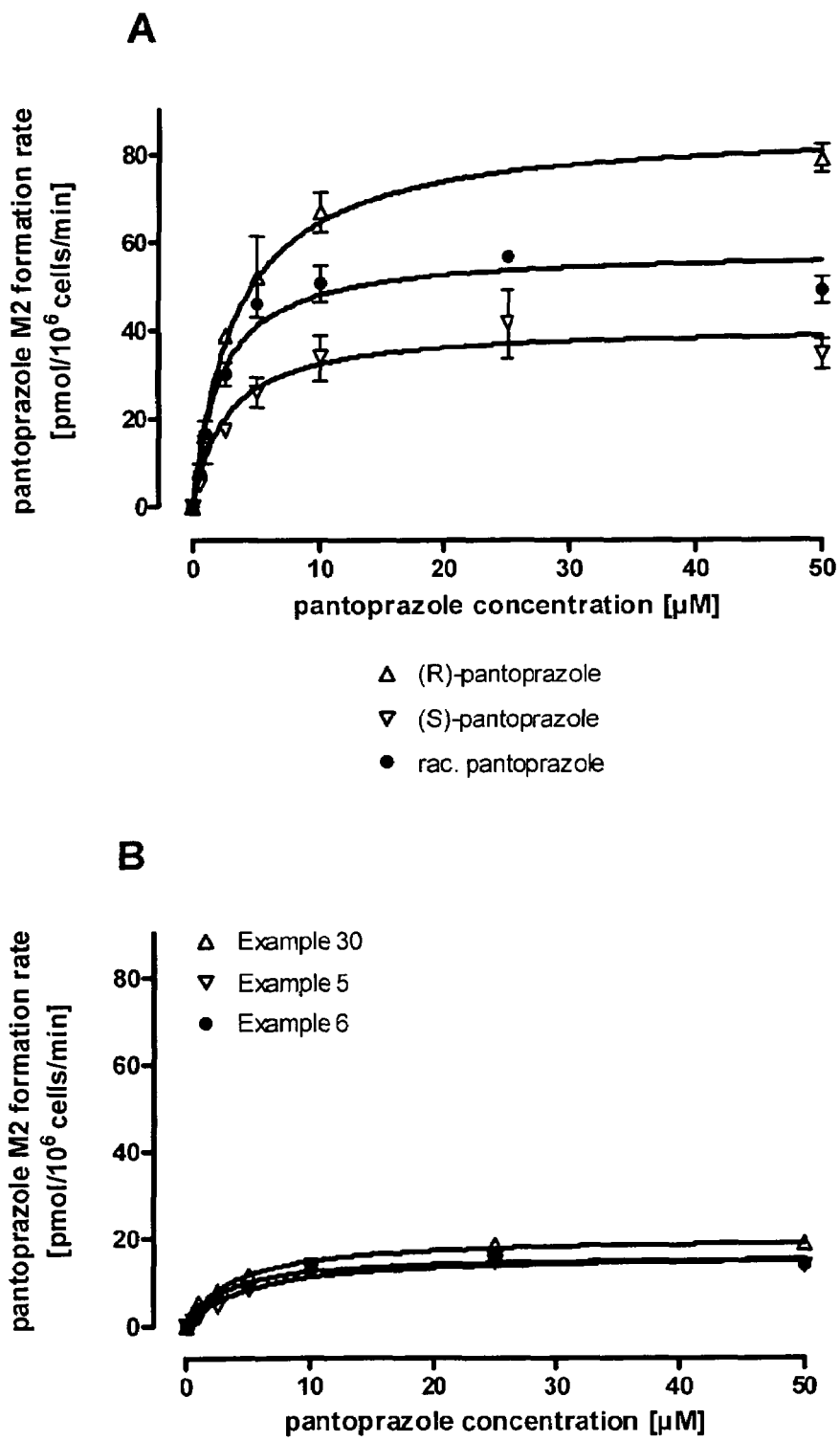
Figure 1: Kinetics of M2 formation from (A) racemic [$^1$H]pantoprazole and enantiomers and (B) [$^2$H$_3$]pantoprazole (example 6) and corresponding enantiomers (examples 5 and 30) in pooled cryopreserved human hepatocytes.

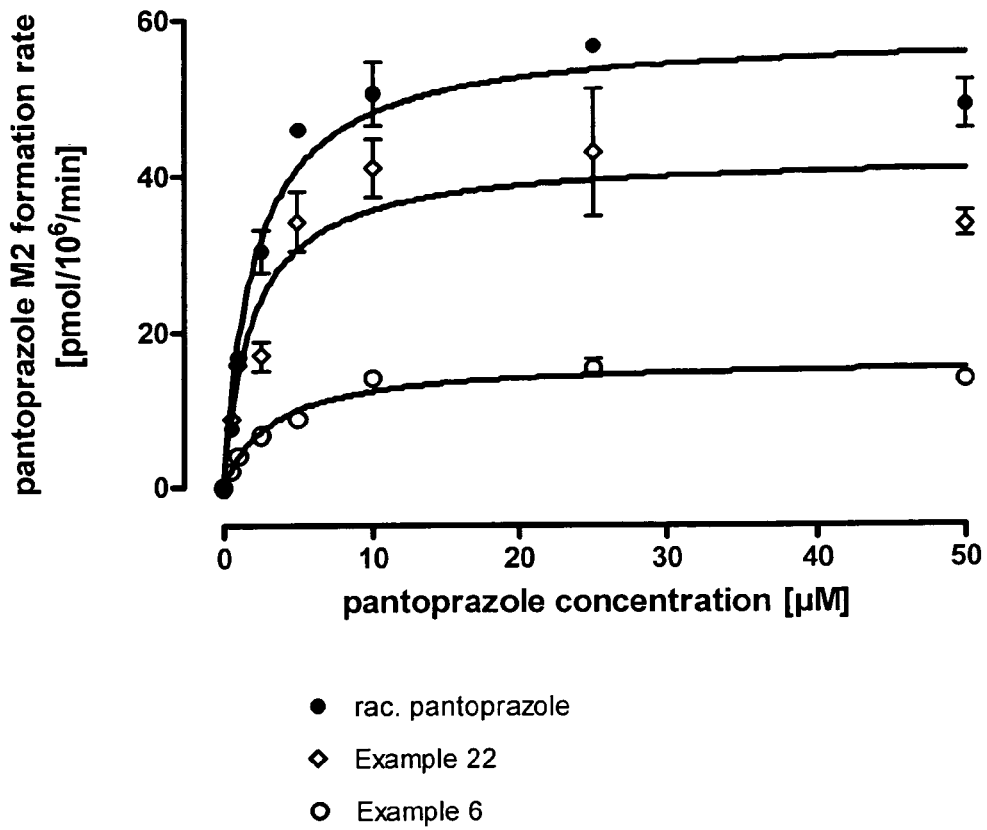
Figure 2: Kinetics of M2 formation rates from rac. [$^1$H]pantoprazole and [$^2$H$_3$] analogues deuterated in the 4-methoxy-pyridyl (example 6) or 3-methoxy-pyridyl position (example 22) in pooled cryopreserved human hepatocytes.

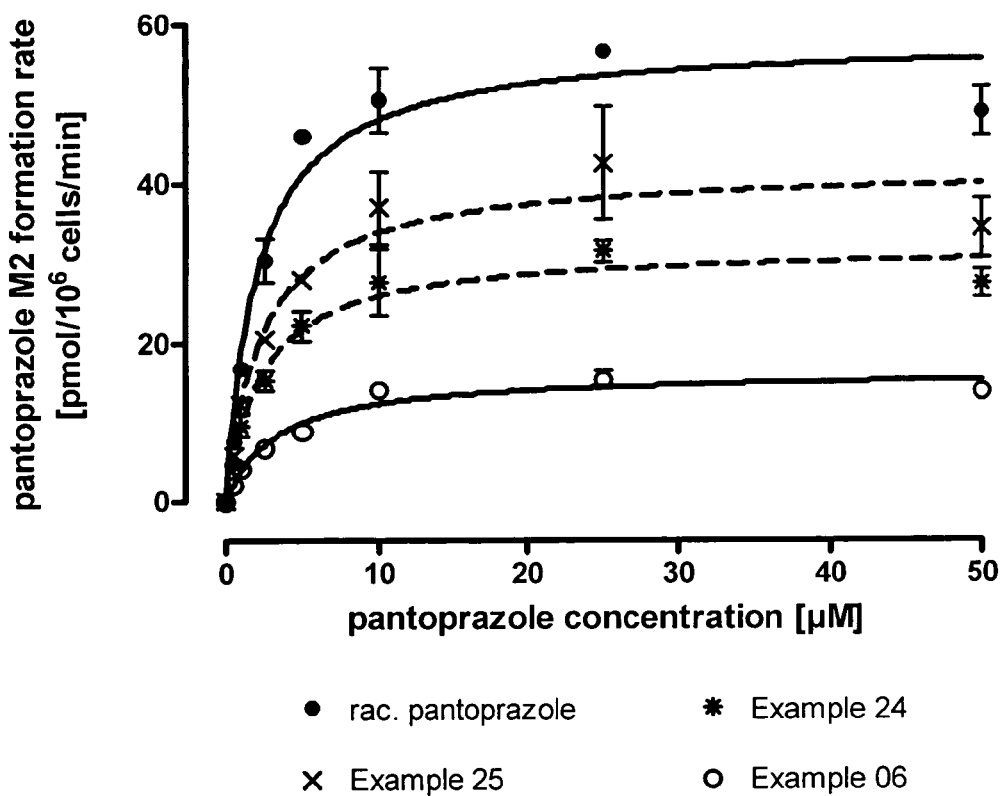
Figure 3: [$^2$H] isotope effect on the kinetics of M2 formation rates from racemic pantoprazole analogues ([$^1$H]pantoprazole, examples 25, 24 and 6) in pooled cryopreserved human hepatocytes

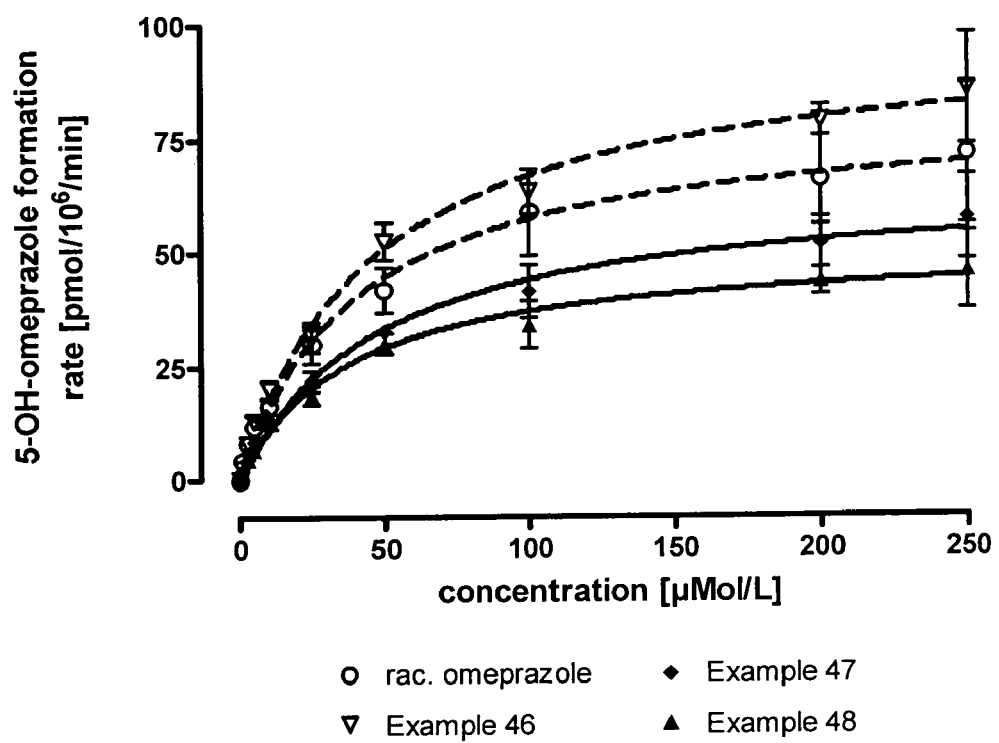
Figure 4: Kinetics of 5-hydroxy-omeprazole formation from [1H]omeprazole and examples 46, 47, and 48.

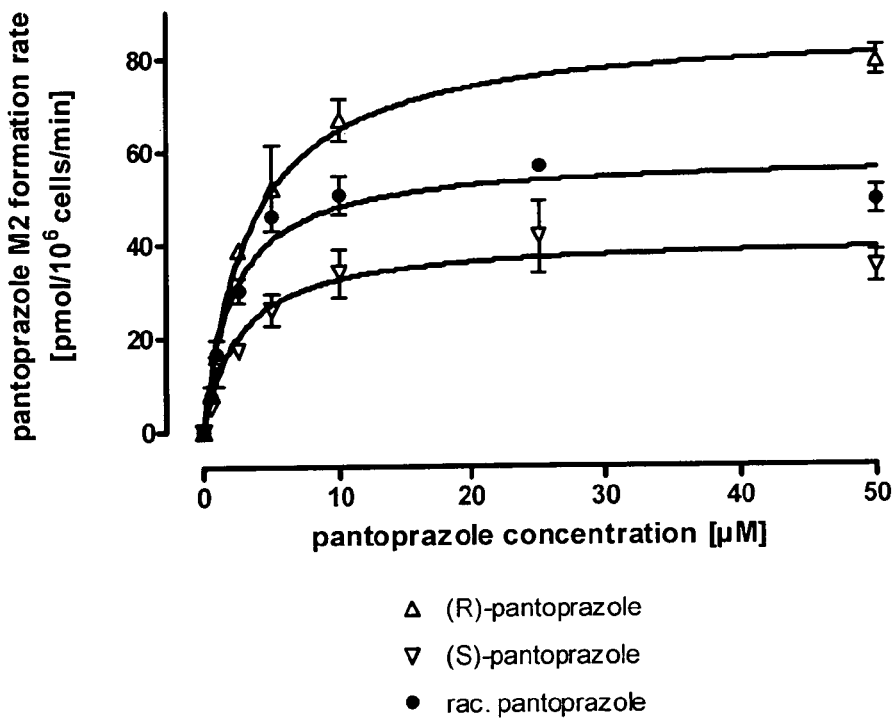
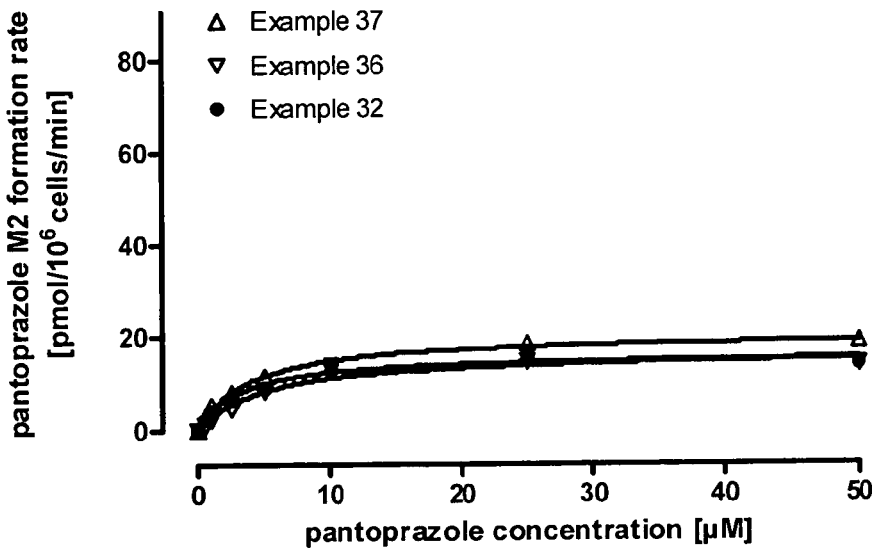
Figure 5: Kinetics of M2 formation from (A) racemic [$^1$H]pantoprazole and enantiomers and (B) [$^2$H$_3$]pantoprazole (example 32) and corresponding enantiomers (examples 36 and 37) in pooled cryopreserved human hepatocytes.

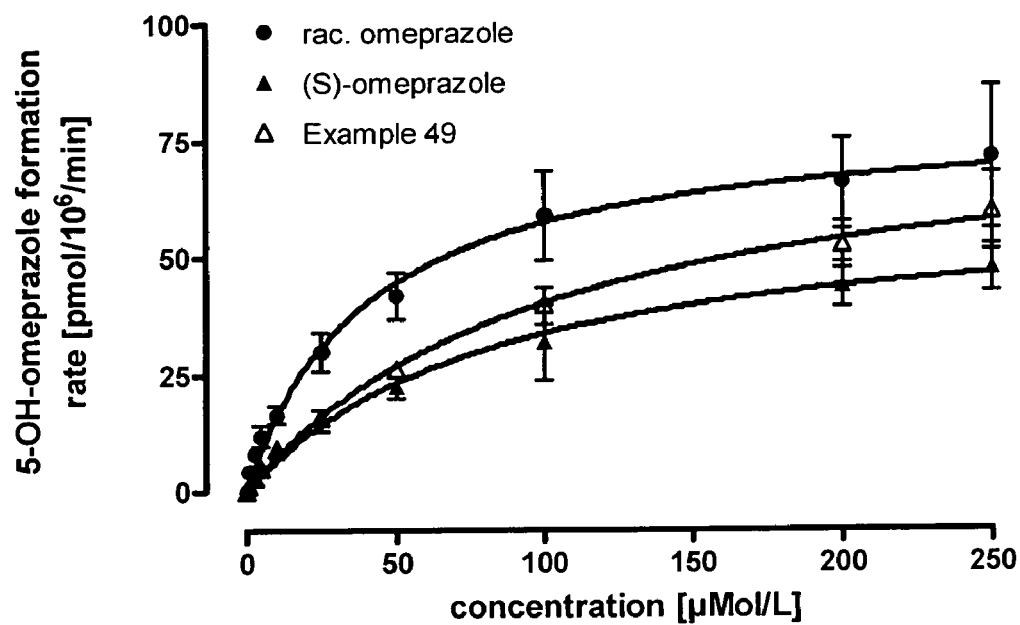
Figure 6: Kinetics of 5-hydroxy-omeprazole formation rates from rac. [$^1$H]omeprazole, (S)-[$^1$H]omeprazole and example 49 in pooled cryopreserved human hepatocytes.

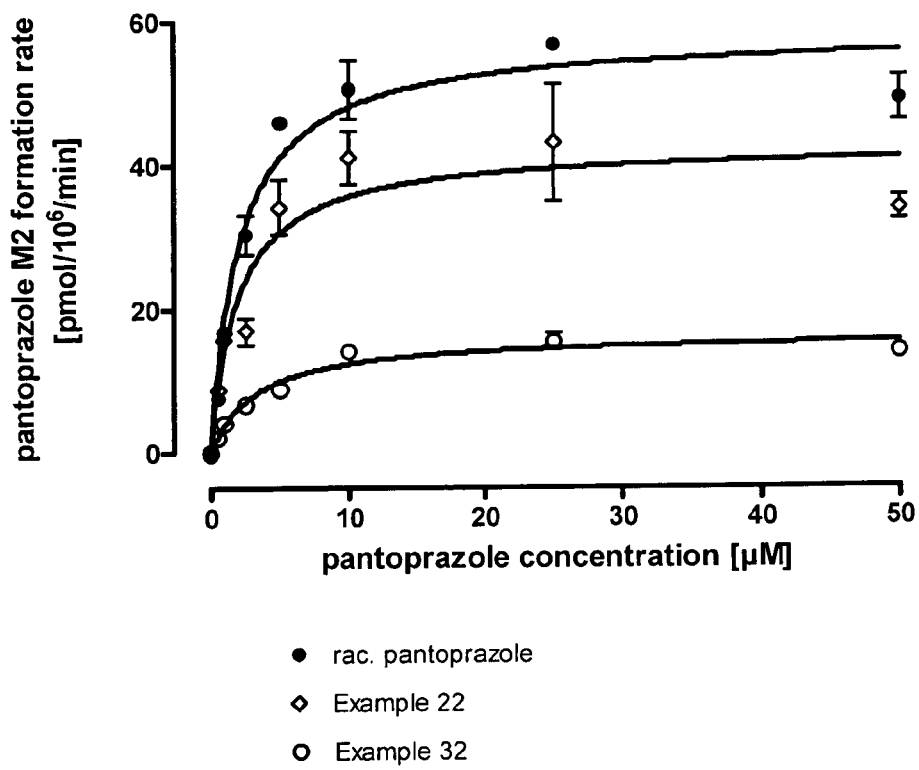
Figure 7: Kinetics of M2 formation rates from rac. [$^1$H]pantoprazole and [$^2$H$_3$] analogues deuterated in the 4-methoxy-pyridyl (example 32) or 3-methoxy-pyridyl position (example 22) in pooled cryopreserved human hepatocytes.

ISOTOPICALLY SUBSTITUTED PROTON PUMP INHIBITORS

SUBJECT MATTER OF THE INVENTION

The present invention relates to isotopically substituted proton pump inhibitors and their (R)- and (S)-enantiomers. These compounds can be used in the pharmaceutical industry for preparing pharmaceutical compositions.

BACKGROUND OF THE INVENTION

Owing to their $H^+/K^+$-ATPase-inhibitory action, pyridin-2-ylmethylsulphinyl-1H-benzimidazoles, such as those known, for example, from EP-A-0005129, EP-A-0166287, EP-A-0174726, EP-A-0254588 and EP-A-0268956 are of considerable importance in the therapy of disorders associated with an increased secretion of gastric acid.

Examples of active compounds from this group which are commercially available or in clinical development are 5-methoxy-2-[(4-methoxy-3,5-dimethyl-2-pyridinyl)methylsulphinyl]-1H-benzimidazole (INN: omeprazole), (S)-5-methoxy-2-[(4-methoxy-3,5-dimethyl-2-pyridinyl)methylsulphinyl]-1H-benzimidazole (INN: esomeprazole), 5-difluoromethoxy-2-[(3,4-dimethoxy-2-pyridinyl)methylsulphinyl]-1H-benzimidazole (INN: pantoprazole), 2-[3-methyl-4-(2,2,2-trifluoroethoxy)-2-pyridinyl)methylsulphinyl]-1H-benzimidazole (INN: lansoprazole), 2-{[4-(3-methoxypropoxy)-3-methylpyridin-2-yl]methylsulphinyl}-1H-benzimidazole (INN: rabeprazole) and 5-methoxy-2-((4-methoxy-3,5-dimethyl-2-pyridylmethyl)sulphinyl)-1H-imidazo[4,5-b]pyridine (INN: tenatoprazole).

The above mentioned sulphinyl derivatives are, owing to their mechanism of action, also referred to as proton pump inhibitors or, abbreviated, as PPI.

BRIEF DESCRIPTION OF THE DRAWINGS

FIGS. 1A and 1B represent the kinetics of M2 formation from (A) racemic [$^1$H] pantoprazole and enantiomers and (B) [$^2$H$_3$] pantoprazole (example 6) and corresponding enantiomers (examples 5 and 30) in pooled cryopreserved human hepatocytes.

FIG. 2 represents the kinetics of M2 formation rates from racemic [$^1$H] pantoprazole and [$^2$H$_3$] analogues deuterated in the 4-methoxy-pyridyl (example 6) or 3-methoxy-pyridyl position (example 22) in pooled cryopreserved human hepatocytes.

FIG. 3 represents the [$^2$H] isotope effect on the kinetics of M2 formation rates from racemic pantoprazole analogues ([$^1$H] pantoprazole, examples 25, 24 and 6) in pooled cryopreserved human hepatocytes.

FIG. 4 represents the kinetics of 5-hydroxy-omeprazole formation from [$^1$H]omeprazole and examples 46, 47 and 48.

FIGS. 5A and 5B represent the kinetics of M2 formation from (A) racemic [$^1$H] pantoprazole and enantiomers and (B) [$^2$H$_3$] pantoprazole (example 32) and corresponding enantiomers (examples 36 and 37) in pooled cryopreserved human hepatocytes.

FIG. 6 represents the kinetics of 5-hydroxy-omeprazole formation from [1H]omeprazole, (S)-[1 H]omeprazole and example 49 in pooled cryopreserved human hepatocytes.

FIG. 7 represents the kinetics of M2 formation rates from racemic [$^1$H] pantoprazole and [$^2$H$_3$] analogues deuterated in the 4-methoxy-pyridyl (example 32) or 3-methoxy-pyridyl position (example 22) in pooled cryopreserved human hepatocytes.

DESCRIPTION OF THE RELATED ART

U.S. Pat. No. 6,818,200 discloses dihydropyridine compounds and antibiotics wherein at least one hydrogen atom is replaced by a deuterium atom. The deuterated compounds are obtained by reacting the H-form with mixtures of deuterium oxide and a suitable catalyst in sealed vessels at drastic reaction conditions, i.e. at elevated temperatures (60-80° C.) and for prolonged reaction times (up to 190 hours). It further discloses some influence on the pharmacological properties of these compounds due to the H/D exchange.

DISCLOSURE OF THE INVENTION

It has now surprisingly been found that isotopically substituted compounds as disclosed in detail below influences significantly the inhibition of acid secretion.

The invention relates to compounds of the general formula 1

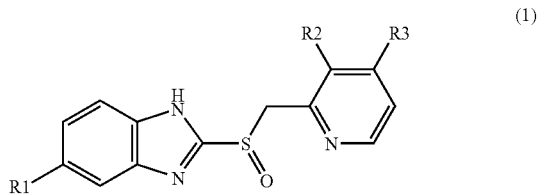

(1)

in which R1 is difluormethoxy, R2 is methoxy, R3 is methoxy and salts, solvates, preferably hydrates and solvates of the salts, preferably hydrates of the salts thereof, wherein at least one of the hydrogen atoms of R1, R2, R3 or any combination of R1, R2 and R3 is replaced by a deuterium atom. Possible combinations are R1 and R2, R1 and R3, R2 and R3 or R1 and R2 and R3.

Preferred within the scope of the invention are compounds wherein at least one of the hydrogen atoms of R2, R3 or R2 and R3 is replaced by a deuterium atom.

Also preferred are compounds wherein R1 is deuteriodifluoromethoxy. Examples of such compounds may be 5-difluoromethoxy-2-[(3-methoxy-4-monodeuteriomethoxy)-2-pyridinyl)methylsulfinyl]-1H-benzimidazole, 5-difluoromethoxy-2-[(3-methoxy-4-dideuteriomethoxy)-2-pyridinyl)methylsulfinyl]-1H-benzimidazole, 5-difluoromethoxy-2-[3-monodeuteriomethoxy-4-methoxy)-2-pyridinyl)methylsulfinyl]-1H-benzimidazole, 5-difluoromethoxy-2-[(3-dideuteriomethoxy-4-methoxy)-2-pyridinyl)methylsulfinyl]-1H-benzimidazole, 5-difluoromethoxy-2-[(3,4-bis(monodeuteriomethoxy)-2-pyridinyl)methylsulfinyl]-1H-benzimidazole or 5-difluoromethoxy-2-[(3,4-bis(dideuteriomethoxy)-2-pyridinyl)methylsulfinyl]-1H-benzimidazole.

Preferred are further compounds wherein R2, R3 or R2 and R3 is trideuteriomethoxy. More preferred is a compound wherein R3 is trideuteriomethoxy. Examples of such compounds may be 5-difluoromethoxy-2-[(3-trideuteriomethoxy-4-methoxy-2-pyridinyl)methylsulfinyl]-1H-benzimidazole, 5-difluoromethoxy-2-[(3-methoxy-4-trideuteriomethoxy-2-pyridinyl)methylsulfinyl]-1H-benzimidazole or 5-difluoromethoxy-2-[(3,4-bis(trideuteriomethoxy)-2-pyridinyl)methylsulfinyl]-1H-benzimidazole.

Most preferred is a compound wherein R1 is difluoromethoxy, R2 is methoxy and R3 is dideuteriomethoxy or trideuteriomethoxy.

Preferred is the sodium or magnesium salt of a compound of formula 1. Preferably, the sodium salt is a monohydrate salt and, even more preferred, a sesquihydrate salt. Preferably, the magnesium salt is a trihydrate salt and, even more preferred, a dihydrate salt.

The invention also relates to compounds of the general formula 10

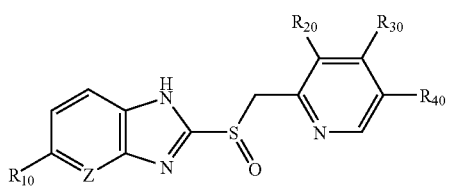

(10)

in which
R10 is hydrogen or 1-4C-alkoxy,
R20 is 1-4C-alkyl or 1-4C-alkoxy,
R30 is 1-4C-alkyl, 1-4C-alkoxy or 2-8C-alkoxyalkoxy,
R40 is hydrogen or 1-4C-alkyl,
Z is C—H or N, and pharmaceutical acceptable salts, solvates, preferably hydrates, and solvates, preferably hydrates of the salts thereof, wherein at least one hydrogen atom of R10, R20, R30, R40 or any combination of R10, R20, R30 and R40 is replaced by a deuterium atom.

Preferred within the scope of the invention are compounds of formula 10 wherein at least one of the hydrogen atoms of R30 is replaced by a deuterium atom and R30 is a 1-2C alkoxy group or a 2-5C-alkoxyalkoxy group.

Preferred are compounds of formula 10 wherein R20 is a 1-4C alkyl group and R30 is a 2-8C-alkoxyalkoxy group, wherein at least one of the hydrogen atoms of R20, R30 or R20 and R30 is replaced by a deuterium atom.

Preferred are compounds of formula 10 wherein R10 is a 1-4C alkoxy group, R20 and R40 are a 1-4C alkyl group and R30 is a 1-4C-alkoxy group, wherein at least one of the hydrogen atoms of R10, R30, R40 or any combination of R10, R30 and R40 is replaced by a deuterium atom.

Preferred are also compounds of formula 10 wherein R10 is hydrogen, methoxy or difluoromethoxy, R20 is methyl or methoxy, R30 is methoxy, 2,2,2-trifluoroethoxy or methoxypropoxy, R40 is hydrogen or methyl and wherein at least one of the hydrogen atoms of R30 is replaced by a deuterium atom.

Preferred are further compounds of formula 10 wherein R20 is methyl, R30 is methoxypropoxy and Z is C—H, wherein at least one of the hydrogen atoms of R20, R30 or R20 and R30 is replaced by a deuterium atom.

Preferred are further compounds of formula 10 wherein R10 is methoxy, R20 and R40 are methyl and R30 is methoxy, wherein at least one of the hydrogen atoms of R10, R30, R40 or any combination of R10, R30 and R40 is replaced by a deuterium atom. Possible combinations are R10 and R30, R10 and R40, R30 and R40, R10 and R30 and R40.

Preferred are also compounds of formula 10 wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein at least one of the hydrogen atoms of R30 is replaced by a deuterium atom.

Preferred are further also compounds of formula 10 wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein at least two of the hydrogen atoms of R30 are replaced by a deuterium atom.

More preferred are compounds of formula 10 wherein R20 is a 1-4C alkyl group and R30 is a 2-8C-alkoxyalkoxy group, wherein all hydrogen atoms of R20, R30 or R20 and R30 are replaced by deuterium atoms.

More preferred are compounds of formula 10 wherein R10 is a 1-4C alkoxy group, R20 and R40 are a 1-4C alkyl group and R30 is a 1-4C-alkoxy group, wherein all hydrogen atoms of R10, R30, R40 or any combination of R10, R30 and R40 are replaced by deuterium atoms. Possible combinations are R10 and R30, R10 and R40, R30 and R40, R10 and R30 and R40.

More preferred are compounds of formula 10 wherein all hydrogen atoms of R30 are replaced by deuterium atoms and wherein R30 is methoxy, 2,2,2-trifluoroethoxy or methoxypropoxy.

More preferred are further compounds of formula 10 wherein R20 is methyl, R30 is methoxypropoxy and Z is C—H, wherein all hydrogen atoms of R20, R30 or R20 and R30 are replaced by deuterium atoms.

More preferred are further compounds of formula 10 wherein R10 is methoxy, R20 and R40 are methyl and R30 is methoxy, wherein all hydrogen atoms of R10, R30, R40 or any combination of R10, R30 and R40 are replaced by deuterium atoms. Possible combinations are R10 and R30, R10 and R40, R30 and R40, R10 and R30 and R40.

More preferred are also compounds of formula 10 wherein R10 is hydrogen, methoxy or difluoromethoxy, R20 is methyl or methoxy, R30 is methoxy, 2,2,2-trifluoroethoxy or methoxypropoxy, R40 is hydrogen or methyl and wherein all hydrogen atoms of R30 are replaced by deuterium atoms.

More preferred are also compounds of formula 10 wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein all hydrogen atoms of R30 are replaced by deuterium atoms.

Most preferred are the compounds 5-methoxy-2-[(4-trideuteriomethoxy-3,5-dimethyl-2-pyridinyl)methylsulphinyl]-1H-benzimidazole, 5-methoxy-2-[(4-dideuteriomethoxy-3,5-dimethyl-2-pyridinyl)methylsulphinyl]-1H-benzimidazole, 5-trideuteriomethoxy-2-[(4-methoxy-3,5-dimethyl-2-pyridinyl)methylsulphinyl]-1H-benzimidazole, 5-trideuteriomethoxy-2-[(4-trideuteriomethoxy-3,5-dimethyl-2-pyridinyl)methylsulphinyl]-1H-benzimidazole, 5-trideuteriomethoxy-2-[(4-dideuteriomethoxy-3,5-dimethyl-2-pyridinyl)methylsulphinyl]-1H-benzimidazole, 5-methoxy-2-[(3-methyl-4-trideuteriomethoxy-5-trideuteriomethyl-2-pyridinyl)methylsulphinyl]-1H-benzimidazole, 5-trideuteriomethoxy-2-[(3-methyl-4-trideuteriomethoxy-5-trideuteriomethyl-2-pyridinyl)methylsulphinyl]-1H-benzimidazole, 2-[3-methyl-4-(1,1-dideuterio-2,2,2-trifluoroethoxy)-2-pyridinyl)methylsulphinyl]-1H-benzimidazole, 5-difluoromethoxy-2-[(3-methoxy-4-trideuteriomethoxy-2-pyridinyl)methylsulphinyl]-1H-benzimidazole, 5-difluoromethoxy-2-[(3-methoxy-4-dideuteriomethoxy-2-pyridinyl)methylsulphinyl]-1H-benzimidazole, 5-difluoromethoxy-2-[(3-trideuteriomethoxy-4-methoxy-2-pyridinyl)methylsulphinyl]-1H-benzimidazole, 5-difluoromethoxy-2-[(3-dideuteriomethoxy-4-methoxy-2-pyridinyl)methylsulphinyl]-1H-benzimidazole, 5-difluoromethoxy-2-[(3,4-bis(trideuteriomethoxy)-2-pyridinyl)methylsulphinyl]-1H-benzimidazole, 5-difluoromethoxy-2-[(3,4-bis(dideuteriomethoxy)-2-pyridinyl)methylsulphinyl]-1H-benzimidazole, 2-{[4-(3-trideuteriomethoxyhexadeuteriopropoxy)-3-methylpyridin-2-yl]methylsulphinyl]-1H-benzimidazole, 2-{[4-(3-trideuteriomethoxyhexadeuteriopropoxy)-3-trideuteriomethylpyridin-2-yl]methylsulphinyl}-1H-benzimidazole, 5-methoxy-2-((4-trideuteriomethoxy-3,5-dimethyl-2-pyridylmethyl)sulphinyl)-1H-imidazo[4,5-b]pyridine, 5-trideuteriomethoxy-2-((4-trideuteriomethoxy-3,5-dimethyl-2-pyridylmethyl)sulphinyl)-1H-imidazo[4,5-b]pyridine, 5-methoxy-2-((3-methyl-4-trideuteriomethoxy-5-trideuteriomethyl-2-pyridylmethyl)sulphinyl)-1H-imidazo[4,5-b]pyridine or 5-trideuteriomethoxy-2-((3-methyl-4-trideuteriomethoxy-5-trideuteriomethyl-2-pyridylmethyl)sulphinyl)-1H-imidazo[4,5-b]pyridine.

1-4C-Alkyl represents straight-chain or branched alkyl groups having 1 to 4 carbon atoms. Examples which may be mentioned are the butyl, isobutyl, sec-butyl, tert-butyl, propyl, isopropyl, ethyl and, preferably, the methyl group.

1-4C-Alkoxy represents a group, which in addition to the oxygen atom contains one of the aforementioned 1-4C-alkyl groups or fluorinated 1-4C-alkyl groups. Examples for 1-4C-alkyl groups which may be mentioned are the butoxy, isobutoxy, sec-butoxy, tert-butoxy, propoxy, isopropoxy, ethoxy and, preferably, the methoxy group. Examples for fluorinated 1-4C-alkyl groups are 2,2,3,3,3-pentafluoropropyl, 2,2,3,3-tetrafluoropropyl, 1-(trifluoromethyl)-2,2,2-trifluoroethyl, 2,2,3,3,4,4,4-heptafluorobutyl and, preferably, 2,2,2-trifluoroethyl and difluoromethyl.

2-8C-Alkoxyalkoxy represents a group, which in addition to the oxygen atom contains an internal alkylene which contains 1-4C alkylene groups and a terminal alkyl group which contains 1-4C alkyl groups and being connected by an oxygen atom to the internal alkylene group. Examples are methoxymethoxy, methoxyethoxy, ethoxymethoxy, ethoxypropoxy, ethoxyisopropoxy, isopropoxymethoxy, propoxymethoxy, methoxybutoxy, methoxyisobutoxy, propoxyethoxy, isopropoxyethoxy, propoxypropoxy, isopropoxyisopropoxy, isopropoxypropoxy, propoxyisopropoxy, ethoxybutoxy, ethoxyisobutoxy, ethoxy-sec-butoxy, ethoxy-tert-butoxy and preferably methoxypropoxy.

According to the invention, within the meaning of salts all salts with inorganic and organic bases are included, in particular the salts with alkali metals, such as the lithium, sodium and potassium salts, or the salts with alkaline earth metals, such as the magnesium and calcium salts, but also other pharmacologically compatible salts, such as, for example, the aluminium or the zinc salts. Particularly preferred are the sodium and the magnesium salts.

Pharmacologically incompatible salts, which can initially be obtained, for example, as process products in the production of the compounds according to the invention on the industrial scale, which are also within the scope of the invention, are—for the production of pharmaceutical compositions—converted into the pharmacologically tolerable salts by processes known to the person skilled in the art.

It is known to the person skilled in the art that the compounds according to the invention and their salts, if, for example, they are isolated in crystalline form, can contain various amounts of solvents. The invention therefore also comprises all solvates and in particular all hydrates of the compounds of the formula 1, and also all solvates and in particular all hydrates of the salts of the compounds of the formula 1. Within the meaning of solvates all pharmaceutically acceptable solvents resulting in such solvates are included.

According to the invention the term "at least one" refers to 1 to 3 hydrogen atoms of R2 or R3, which can be replaced by deuterium atoms.

Concerning the nomenclature of the compounds according to the invention the terms "deutero" or "deuterio" should indicate a deuterium atom ([$^2$H]). Similarly, the pre-terms "bis" or "di" and "tri" or "tris", respectively should indicate the occurrence of two or three, for example deuterio atoms in a specific group, i.e. 1,1-dideuterio-2,2,2-trifluoroethoxy or trideuteriomethoxy.

According to the invention, the term "hydrogen atom replaced by a deuterium atom" has to be understood as defining a degree of deuteration of at least 80% for the bulk material, where all these correspondingly mentioned hydrogen atoms are replaced by deuterium atoms. For example, if the substituent R2 or R3 refers to a methoxy group having all three "hydrogen atoms replaced by a deuterium atoms" it is to be understood according to the above definition that at least 80% of all the R2 or R3 methoxy groups in the bulk material are —OCD$_3$. The remaining part up to 100% includes —OCHD$_2$, —OCH$_2$D or —OCH$_3$.

Preferred is a degree of deuteration of at least 90% for the specific hydrogen atom in the bulk material, meaning that at least 90% of the replaced hydrogen atoms should be deuterium atoms. More preferred is a degree of deuteration of at least 92% for the specific hydrogen atom in the bulk material. Even more preferred is a degree of deuteration of at least 94% for the specific hydrogen atom in the bulk material and most preferred is a degree of deuteration of at least 96% for the specific hydrogen atom in the bulk material.

The compounds according to the invention show significant improved properties with respect to the known compounds concerning the influences on secretion of gastric acid.

The compounds according to the invention are chiral compounds. The invention thus relates to the racemates as well as to the enantiomers and mixtures thereof in any desired ratio. In view of the fact that, from a medicinal point of view, it may be advantageous for certain chiral compounds to be administered in the form of the one or the other enantiomer, a preferred subject matter of the inventions are the enantiomers of the compounds of formulae 1 and 10, preferably the enantiomers being substantially free of the respective other enantiomer with opposite configuration.

Accordingly, particularly preferred are on one hand the compounds with (S)-configuration of the general formula 1a

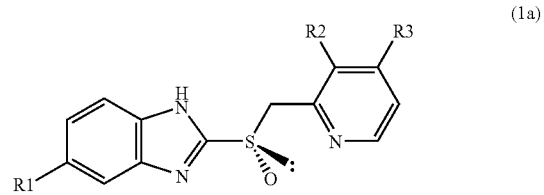

(1a)

in which R1, R2 and R3 have the meanings given above.

A particularly preferred compound with (S)-configuration within the scope of the invention is the compound (S)-5-difluoromethoxy-2-[(3-methoxy-4-trideuteriomethoxy-2-pyridylmethyl)sulphinyl]-1H-benzimidazole and the solvates, preferably hydrates of this compound, the salts of this compound and the solvates, preferably hydrates of the salts of this compound. Another particularly preferred compound with (S)-configuration within the scope of the invention is the compound (S)-5-difluoromethoxy-2-[(3-methoxy-4-dideuteriomethoxy-2-pyridylmethyl)sulphinyl]-1H-benzimidazole and the solvates, preferably hydrates of this compound, the salts of this compound and the solvates, preferably hydrates of the salts of this compound.

Preferred is the sodium or magnesium salt of a compound of formula 1a. Preferably, the sodium salt or the magnesium salt of the S-enantiomer is a trihydrate.

Particularly preferred are on the other hand the compounds with (R)-configuration of the general formula 1b

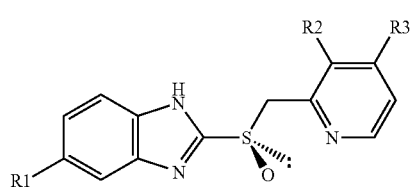

(1b)

in which R1, R2 and R3 have the meanings given above.

A particularly preferred compound with (R)-configuration within the scope of the invention is the compound (R)-5-difluoromethoxy-2-[(3-methoxy-4-trideuteriomethoxy-2-pyridylmethyl)sulphinyl]-1H-benzimidazole and the solvates, preferably hydrates of this compound, the salts of this compound and the solvates, preferably hydrates of the salts of this compound. Another particularly preferred compound with (R)-configuration within the scope of the invention is the compound (R)-5-difluoromethoxy-2-[(3-methoxy-4-dideuteriomethoxy-2-pyridylmethyl)sulphinyl]-1H-benzimidazole and the solvates, preferably hydrates of this compound, the salts of this compound and the solvates, preferably hydrates of the salts of this compound.

Further, particularly preferred are on one hand the compounds with (S)-configuration of the general formula 10a

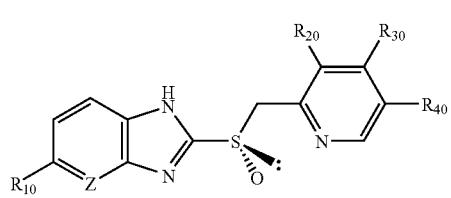

(10a)

in which R10, R20, R30, R40 and Z have the meanings given above.

Particularly preferred compounds with (S)-configuration within the scope of the invention are the compounds (S)-5-methoxy-2-[(4-trideuteriomethoxy-3,5-dimethyl-2-pyridinyl)methylsulphinyl]-1H-benzimidazole, (S)-5-trideuteriomethoxy-2-[(4-trideuteriomethoxy-3,5-dimethyl-2-pyridinyl)methylsulphinyl]-1H-benzimidazole, (S)-5-methoxy-2-[(4-dideuteriomethoxy-3,5-dimethyl-2-pyridinyl)methylsulphinyl]-1H-benzimidazole, (S)-5-trideuteriomethoxy-2-[(4-dideuteriomethoxy-3,5-dimethyl-2-pyridinyl)methylsulphinyl]-1H-benzimidazole, (S)-5-trideuteriomethoxy-2-[(4-methoxy-3,5-dimethyl-2-pyridinyl)methylsulphinyl]-1H-benzimidazole, (S)-5-methoxy-2-[(3-methyl-4-trideuteriomethoxy-5-trideuteriomethyl-2-pyridinyl)methylsulphinyl]-1H-benzimidazole, (S)-5-trideuteriomethoxy-2-[(3-methyl-4-trideuteriomethoxy-5-trideuteriomethyl-2-pyridinyl)methylsulphinyl]-1H-benzimidazole or (S)-5-difluoromethoxy-2-[(3-methoxy-4-trideuteriomethoxy-2-pyridylmethyl)sulphinyl]-1H-benzimidazole, (S)-5-difluoromethoxy-2-[(3-methoxy-4-dideuteriomethoxy-2-pyridylmethyl)sulphinyl]-1H-benzimidazole and the solvates, preferably hydrates of these compounds, the salts of these compounds and the solvates, preferably hydrates of the salts of these compounds.

Particularly preferred are on the other hand the compounds with (R)-configuration of the general formula 10b

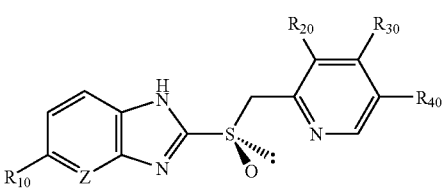

(10b)

in which R10, R20, R30, R40 and Z have the meanings given above.

A particularly preferred compound with (R)-configuration within the scope of the invention is the compound (R)-5-difluoromethoxy-2-[(3-methoxy-4-trideuteriomethoxy-2-pyridylmethyl)sulphinyl]-1H-benzimidazole, (R)-5-difluoromethoxy-2-[(3-methoxy-4-dideuteromethoxy-2-pyridylmethyl)sulphinyl]-1H-benzimidazole and the solvates, preferably hydrates of these compounds, the salts of these compounds and the solvates, preferably hydrates of the salts of these compounds.

The separation of the compounds of formula 1 and formula 10 into the enantiomers can be accomplished according to various processes, for example as described in international patent application WO92/08716 or by column chromatography. Alternatively, the compounds of formulae 1a and 1b, as well as the compounds of formulae 10a and 10b can be obtained by chiral oxidation of the sulphides as described in international patent applications WO96/02535 or WO 2004/052881.

The salts of the compounds of formulae 1, 1a and 1b, as well as compounds of formulae 10, 10a and 10b are prepared by processes known per se by reacting the compounds of formulae 1, 1a, 1b, 10, 10a and 10b, which can be regarded as weak acids, with suitable bases, for example with alkali metal hydroxides or alkoxides, such as sodium hydroxide or sodium methoxide, or with alkaline earth metal alkoxides, such as magnesium methoxide. As an example, the magnesium salts of the compounds of formulae 1, 1a, 1b, 10, 10a and 10b, which are—besides the sodium salts—the preferred salts, are prepared in a manner known per se by reacting compounds of formulae 1, 1a, 1b, 10, 10a and 10b with a magnesium base, for example a magnesium alkoxide, or from a readily soluble salt of a compound of formulae 1, 1a, 1b, 10, 10a and 10b (for example of a sodium salt) using a magnesium salt in water or in mixtures of water with polar organic solvents (for example alcohols, preferably methanol, ethanol or isopropanol, or ketones, preferably acetone).

According to the invention, "compounds with (S)-configuration" is understood to include "compounds with (S)-configuration being substantially free of compounds with (R)-configuration".

"Substantially free" in the context of the invention means that the compounds with (S)-configuration and/or their salts, solvates or solvates of salts contain less than 10% by weight of compounds with (R)-configuration and/or their salts, solvates or solvates of salts. Preferably, "substantially free" means that compounds with (S)-configuration and/or their salts, solvates or solvates of salts contain less than 5% by weight of compounds with (R)-configuration and/or their salts, solvates or solvates of salts. More preferably, "substantially free" means that compounds with (S)-configuration and/or their salts, solvates or solvates of salts contain less than 2% by weight of compounds with (R)-configuration and/or their salts, solvates or solvates of salts. In the most preferred embodiment, "substantially free" means that compounds with (S)-configuration and/or their salts, solvates or solvates of salts contain less than 1% by weight of compounds with (R)-configuration and/or their salts, solvates or solvates of salts.

According to the invention, "compounds with (R)-configuration" is understood to include "compounds with (R)-configuration being substantially free of compounds with (S)-configuration".

"Substantially free" in the context of the invention means that the compounds with (R)-configuration and/or their salts, solvates or solvates of salts contain less than 10% by weight of compounds with (S)-configuration and/or their salts, solvates or solvates of salts. Preferably, "substantially free" means that compounds with (R)-configuration and/or their salts, solvates or solvates of salts contain less than 5% by weight of compounds with (S)-configuration and/or their salts, solvates or solvates of salts. More preferably, "substantially free" means that compounds with (R)-configuration and/or their salts, solvates or solvates of salts contain less than 2% by weight of compounds with (S)-configuration and/or their salts, solvates or solvates of salts. In the most preferred embodiment, "substantially free" means that compounds with (R)-configuration and/or their salts, solvates or solvates of salts contain less than 1% by weight of compounds with (S)-configuration and/or their salts, solvates or solvates of salts.

Additional subject matter of the invention are compounds of formula 2

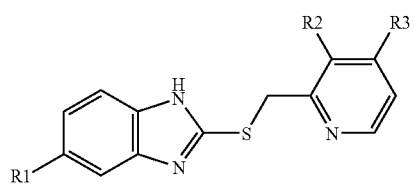

(2)

in which R1, R2 and R3 have the meanings as given above and wherein at least one of the hydrogen atoms of R1, R2, R3 or any combination of R1, R2 and R3 is replaced by a deuterium atom. Possible combinations are R1 and R2, R1 and R3, R2 and R3 or R1 and R2 and R3. The compounds of formula 2 include further their salts with acid, preferably the hydrochloride, the sulphate or the phosphate salts, and/or solvates. These compounds can be used for the manufacture of compounds of general formula 1, 1a or 1b. The compounds of formula 2 are suitable especially as starting material for an oxidation reaction resulting in compounds according formulae 1, 1a or 1b.

Another aspect of the invention are compounds of formula 3

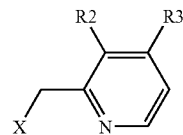

(3)

in which X is a halogen or an activated derivative of an alcohol and R2 and R3 have the meanings as given above and wherein at least one of the hydrogen atoms of R2, R3 or R2 and R3 is replaced by a deuterium atom.

For the purpose of the invention, halogen is iodine, bromine, chlorine and fluorine. Preferably X is chlorine. For the purpose of the invention, an activated derivate of an alcohol is an alkylsulfonate group, for example mesylate or an arylsulfonate group, for example tosylate or besylate, or a perfluoroalkanesulfonate group, for example trifluoromethanesulfonate.

The compounds of formula 3 can be used for the manufacture of compounds of formula 1, 1a or 1b. Preferably the nitrogen atom of compound of formula 3 is first quaternised and then reacted with compounds of formula 4

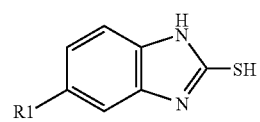

(4)

in which R1 has the meaning as given above, thus providing compounds of formula 2 as described above.

The deuterium homologes of R/S pantoprazole and S-pantoprazole can be prepared by oxidation of the corresponding thio-compounds according to methods known from literature, e.g. Kohl et al. J. Med. Chem. 1992, 35, 1049 ff. or WO 2004/052881 or by exchange of halogen for trideuteriomethoxy from the corresponding sulfoxides with a halogen (e.g. chloro, bromo or nitro) substituent at the position of the final trideuteriomethoxy group, in particular in 4-position of the pyridine group.

In analogy the thiocompounds are prepared either by exchange of halogen by trideuteriomethoxy at the position of the final trideuteriomethoxy-substituent or by coupling of 5-difluoromethoxy-2-mercaptobenzimidazole with the accordingly substituted 2-chloromethyl-3-methoxy-4-trideuteriomethoxy-pyridinumchloride. The disclosed preparation routes can also be used to substitute the halogen by dideuteriomethoxy or monodeuteriomethoxy instead of trideuteriomethoxy as described above. These syntheses will lead to the correspondingly deuterated compounds.

The compound of formula 1 can be prepared according to the following reaction scheme:

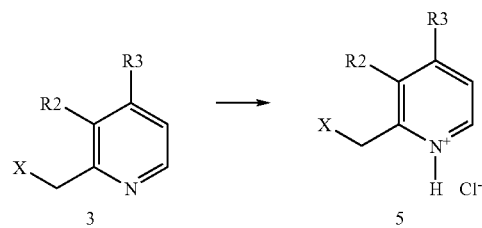

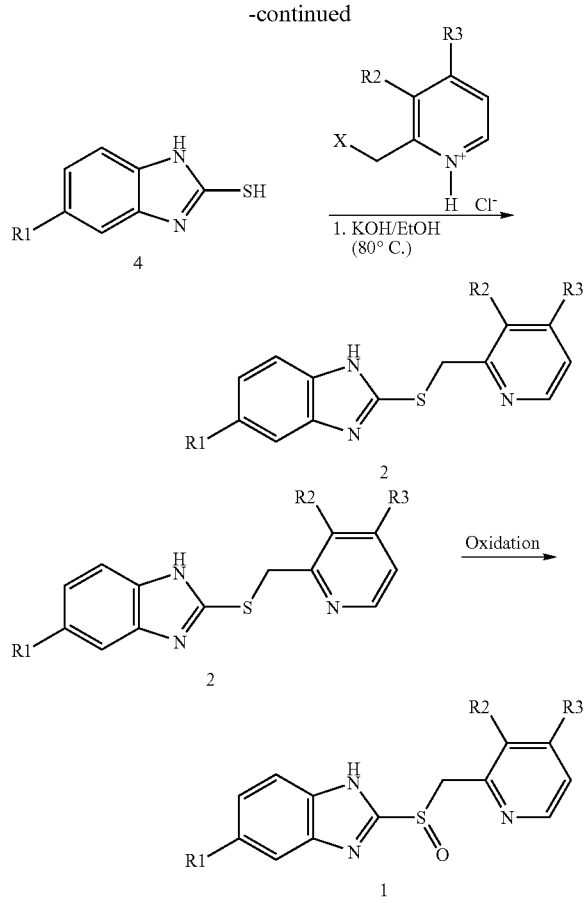

Salts of the sulfoxides with anorganic bases are prepared according to methods known from literature by reaction of the sulfoxides with the corresponding hydroxides or alkoxides in organic solvents or mixtures of organic solvents with water.

Alternatively salts are prepared by reaction of sulfoxides with alkali hydroxides to give the corresponding alkali salt (Na, K, Li) and further reaction with e.g. magnesium, calcium, aluminum, zinc salts.

Additional subject matter of the invention are compounds of formula 20

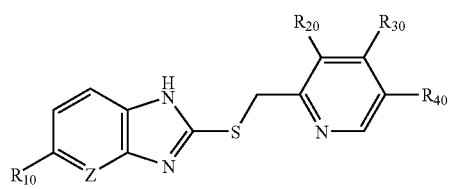

in which R10, R20, R30, R40 and Z have the meanings as given above and wherein at least one of the hydrogen atoms of R10, R20, R30, R40 or any combination of R10, R20, R30 and R40 is replaced by a deuterium atom, and their salts, such as the hydrochloride, the sulfate, the phosphate or other salts with acids, and their solvates. These compounds can be used for the manufacture of compounds of general formula 10, 10a or 10b. The compounds of formula 20 are suitable especially as starting material for an oxidation reaction resulting in compounds according formulae 10, 10a or 10b.

Another aspect of the invention are compounds of formula 30

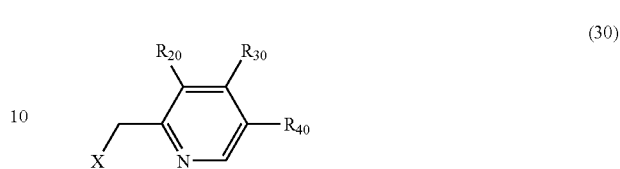

in which X is a halogen or an activated derivative of an alcohol and R20, R30 and R40 have the meanings as given above and wherein at least one of the hydrogen atoms of R20, R30 and/or R40 is replaced by a deuterium atom.

Preferred are compounds of formula 30 wherein R20 is methyl or methoxy, R30 is methoxy, 2,2,2-trifluoroethoxy or methoxypropoxy, R40 is hydrogen or methyl and wherein at least one of the hydrogen atoms of R30 is replaced by deuterium atoms.

More preferred are compounds of formula 30 wherein R20 is methyl, R30 is methoxy, R40 is methyl or R20 is methoxy, R30 is methoxy, R40 is hydrogen or R20 is methyl, R30 is 2,2,2-trifluoroethoxy or methoxypropoxy, R40 is hydrogen and wherein at least one of the hydrogen atoms of R30 is replaced by deuterium atoms.

Also more preferred are compounds of formula 30 wherein R20 is methyl, R30 is methoxy, R40 is methyl or R20 is methoxy, R30 is methoxy, R40 is hydrogen or R20 is methyl, R30 is 2,2,2-trifluoroethoxy or methoxypropoxy, R40 is hydrogen and wherein at least two or all of the hydrogen atoms of R30 are replaced by deuterium atoms.

For the purpose of the invention, halogen is iodine, bromine, chlorine and fluorine. Preferably X is chlorine. An activated derivative of an alcohol is an alkylsulfonate group, for example mesylate or an arylsulfonate group, for example tosylate or besylate, or a perfluoroalkanesulfonate group, for example trifluormethanesulfonate.

Related to a compound of formula 30 and thus an aspect of the invention is a compound of formula 30a

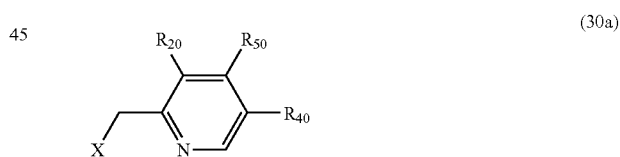

in which X, R20 and R40 have the meanings as given above, R50 being chloro or nitro and wherein at least one of the hydrogen atoms of R20 and/or R40 is replaced by a deuterium atom.

Preferred are compounds of formula 30a wherein R20 is methyl or methoxy, R40 is hydrogen or methyl and wherein at least one of the hydrogen atoms of R20 and/or R40 is replaced by deuterium atoms.

More preferred are compounds of formula 30a wherein R20 and R40 are methyl and wherein at least one of the hydrogen atoms of R20 and/or R40 is replaced by deuterium atoms.

The compounds of formula 30 can be used for the manufacture of compounds of formula 10, 10a or 10b. Preferably the nitrogen atom of compound of formula 30 is first quaternised and then reacted with compounds of formula 40

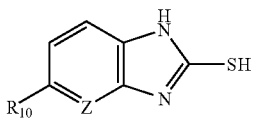

in which R10 and Z have the meaning as given above, thus providing compounds of formula 20 as described above.

The compounds of formula 30a can be used for the manufacture of compounds of formula 20a.

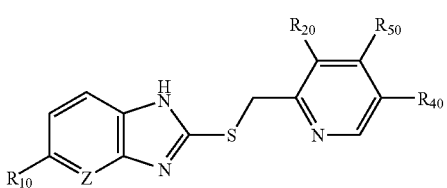

in which R10, R20, R50, R40 and Z have the meanings as given above and wherein at least one of the hydrogen atoms of R10, R20, R40 or any combination of R10, R20 and R40 is replaced by a deuterium atom.

Preferably the nitrogen atom of compound of formula 30a is first quaternised and then reacted with compounds of formula 40

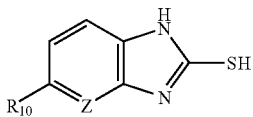

in which R10 and Z have the meaning as given above, thus providing compounds of formula 20a as described above.

Compounds of formula 20a can be used for the manufacturing of compounds of formula 20 by substituting the residue R50 with a residue R30, both having the meanings as described above. Under the proviso that none of the hydrogens of R10, R20 or R40 are replaced by a deuterium atom, at least one of the hydrogen atoms of R30 is replaced by a deuterium atom.

Another aspect of the invention are compounds of formula 40

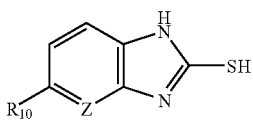

wherein R10 is 1-4C alkoxy, Z is C—H or N and wherein at least one of the hydrogen atoms of R10 is replaced by a deuterium atom. Preferably R10 is methoxy. These compounds may be used for the manufacture of compounds of formula 10 or 20.

More preferred are compounds wherein R10 is methoxy and wherein all hydrogen atoms of R10 are replaced by deuterium atoms.

The deuterium homologes of the proton pump inhibitors and for example of R/S pantoprazole and S-pantoprazole are prepared by oxidation of the corresponding thio-compounds according to methods known from literature, e.g. Kohl et al. J. Med. Chem. 1992, 35, 1049 ff. or WO 2004/052881 or by exchange of halogen for trideuteriomethoxy from the corresponding sulfoxides with a halogen (e.g. chloro, bromo or nitro) substituent at the position of the final trideuteriomethoxy group, in particular in 4-position of the pyridin group. Similar as described before an exchange of the halogen by dideuteriomethoxy or monodeuteriomethoxy will lead to the correspondingly deuterated compounds.

In analogy the thiocompounds are prepared either by exchange of halogen by mono-, di- or trideuteriomethoxy at the position of the final mono-, di- or trideuteriomethoxy-substituent or by coupling of 5-difluoromethoxy-2-mercaptobenzimidazole with the accordingly substituted 2-chloromethyl-3-methoxy-4-trideuteriomethoxy-pyridinumchloride.

The compound of formula 10 can be prepared according to the following reaction scheme:

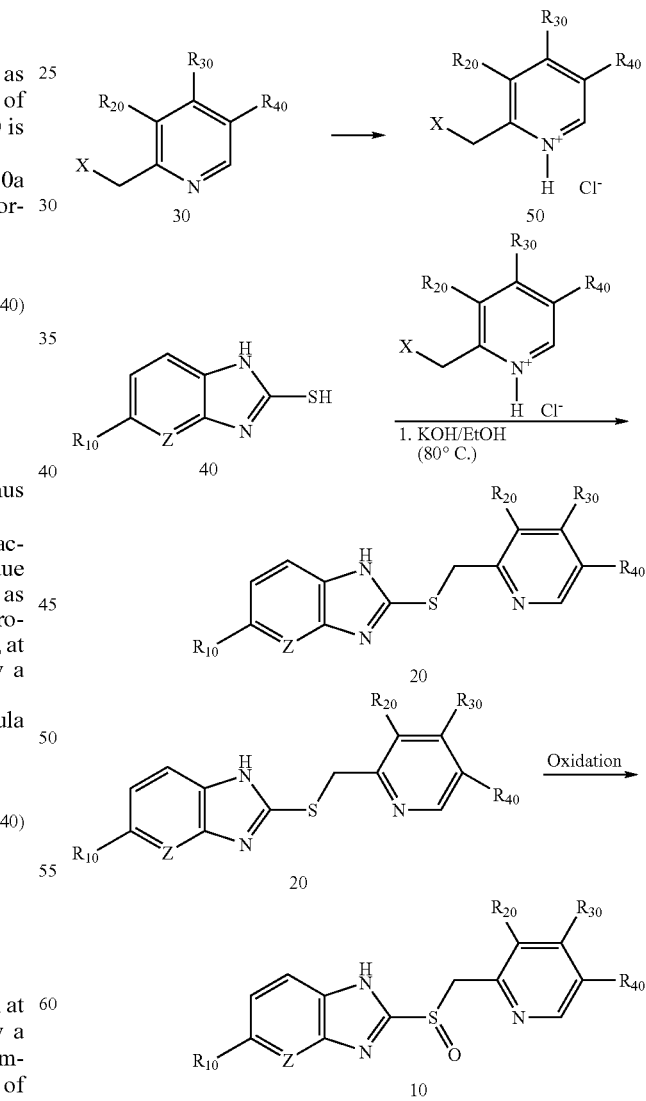

Salts of the sulfoxides with anorganic bases are prepared according to methods known from literature by reaction of the sulfoxides with the corresponding hydroxides or alkoxides in organic solvents or mixtures of organic solvents with water.

Alternatively salts are prepared by reaction of sulfoxides with alkali hydroxides to give the corresponding alkali salt (Na, K, Li) and further reaction with e.g. magnesium, calcium, aluminum, zinc salts.

The following examples serve to illustrate the invention in greater detail without restricting it to the described examples. The other above mentioned compounds can be obtain by using the described methods.

EXAMPLES

As trideuteriomethoxylation agent, methanol-d4 with >99.8 atom % D was used. Isomeric purity of the trideuteriomethoxy substituent(s) in all resulting products was >98.0% as determined by NMR and MS.

As further deuteration agents, methanol-d2 with >98.0 atom % D, and methanol-dl with >98.0 atom % D were used. Isomeric purity of the dideuteriomethoxy and monodeuteriomethoxy substituents in the resulting products was >96.0% as determined by NMR and MS.

Example 1

(R/S)-5-Difluoromethoxy-2-[(3-methoxy-4-trideuteriomethoxy-2-pyridinyl)methylsulfinyl]-1H-benzimidazole A solution of sodium hypochlorite (10% strength) (3.3 mmol) is added over one to two hours to a slurry of 5-difluoromethoxy-2-[(3-methoxy-4-trideuteriomethoxy-2-pyridinyl)methylthio]-1H-benzimidazole (1.0 g, 2.7 mmol) in water (20 mL), 2-propanol (10 mL) and sodium hydroxide (0.5 mL 40% strength solution, 7.1 mmol) at 30-35° C. with stirring. After 30-60 minutes at the stated temperature sodium thiosulfate (0.3 g dissolved in 5 mL of water) is added and stirring is continued for a further 15-30 minutes.

The reaction mixture is concentrated in vacuo (30-40° C.) to about one third of the original volume and water (about 70 mL) is added.

After extraction of the water phase with dichloromethane (2×10 mL each) again dichloromethane (50 mL) is added and the pH is adjusted to 7-8 by addition of aqueous potassium dihydrogenphosphate while stirring. Phase separation, one further extraction of the water phase with dichloromethane (20 mL), washing of the combined organic phases with water (20 mL) drying with magnesium sulfate and filtration of the drying agent gives a solution of the crude title compound.

Addition of petroleum ether (50/70; 150 mL) and concentration in a rotary evaporator in vacuo at 30-40° C. to about 30 mL volume followed by filtration of the precipitated solid, rinse with petroleum ether 50/70 (20 mL) and drying in vacuo (35° C., 5 hours) yields the title compound (R/S)-5-difluoromethoxy-2-[(3-methoxy-4-trideuteriomethoxy-2-pyridinyl)methylsulfinyl]-1H-benzimidazole as an offwhite solid of m. p. 135-136° C. (decomp.); yield 1.0 g (95% of theoretical).

$^1$H-NMR (400 MHz, DMSO d-6): δ=3.78 (s, 3H, OMe), 4.68 (d, 1H, J (CHa, CHb) =13 Hz, S—CH2-Py), 4.73 (d, 1H, J (CHb, CHa)=13 Hz, S—CH2-Py), 7.10 (d, 1H, J(H5', H6')=5 Hz, H5') 7.18 (bd, 1H, H6), 7.24 (t, 1H, J (H, F)=74 Hz, OCHF2), 7.4 (bs, 1H, H4), 7.70 (bs, 1H, H7), 8.15 (d, 1H, J (H6', H5')=5 Hz) H6'), 13.7 (s, 1H, NH).

Example 2

(S)(−)-5-Difluoromethoxy-2-[(3-methoxy-4-trideuteriomethoxy-2-pyridinyl)methylsulfinyl]-1H-benzimidazole At room temperature, 2.0 g of 5-difluoromethoxy-2-[(3-methoxy-4-trideuteriomethoxy-2-pyridinyl)methylthio]-1H-benzimidazole are suspended in 20 mL of methyl isobutyl ketone together with (+)-L-tartaric acid bis-(N-pyrrolidinamide) (2.3 g) and zirconium (IV) n-propoxide (1.0 g, 70% in propanol). The mixture is heated at 40° C. for one hour, resulting in the formation of a solution which is almost clear. After cooling to room temperature, N-ethyldiisopropylamine (0.07 mL) and cumene hydroperoxide (1.05 mL) are added. The mixture is stirred at room temperature until the oxidation has ended (10-24 hours, monitored by TLC). The clear solution is diluted with 10 mL of methyl isobutyl ketone and quenched with 0.08 g of sodium thiosulphate in 14 mL of saturated sodium bicarbonate solution and stirred for a further 2 hours. After phase separation the mixture is washed twice with 5 mL of saturated sodium bicarbonate solution. 15 mL of water are added to the methyl isobutyl ketone phase, and the pH is adjusted to pH=13 using a 40% by weight strength solution of sodium hydroxide. After phase separation, the methyl isobutyl ketone phase is extracted with another 5 mL of water at pH 13. The aqueous phases are combined and, at 40° C., subjected to incipient distillation under reduced pressure. Hyflo Super Cell as filtration aid (0.05 g) is added and after stirring for one hour at 20-25° C. filtered off. At 40-45° C., the crude title compound is precipitated by addition of 10% strength acetic acid to the filtrate to pH=9.0. The mixture is stirred for another 12 hours during which the pH is monitored. The beige crystals are filtered off and washed with 10 mL of water. The title compound is obtained in a yield of about 1.6 g (75% of theory) and an optical purity of >98%.

To increase the purity, (−)-trideuteriopantoprazole is dissolved in water/aqueous sodium hydroxide solution at pH=13 and re-precipitated with acetic acid (10%) at pH=9.0.

Recrystallisation from dichloromethane/tert-butylmethylether gives the title compound S(−)-5-difluoromethoxy-2-[(3-methoxy-4-trideuteriomethoxy-2-pyridinyl)methylsulphinyl]-1H-benzimidazole as an offwhite solid of m. p. 146-148° C. (decomp.); yield. 1.6 g.

Example 3

5-Difluoromethoxy-2-[(3-methoxy-4-trideuteriomethoxy-2-pyridinyl)methylthio]-1H-benzimidazole 2-[(4-chloro-3-methoxy-2-pyridinyl)-methylthio]-5-difluoromethoxy-1H-benzimidazole (20 g) is added in four portions over 30-60 minutes at 50-60° C. to a solution of sodium trideuteriomethanolate (prepared from deuteromethanol D4 (7.8 g) and sodium hydride (8.6 g, 60% strength in paraffin) in N-methyl-pyrrolidin-2-one (150 mL).

After four hours at the stated temperature the reaction mixture is cooled to 20-25° C. and water (500 mL) is added over 1-2 hours while stirring. After adjustment to pH 7 with 2N aqueous hydrochloric acid the mixture is stirred for a further hour at 20-25° C.

The precipitate is filtered off over a suction filter, rinsed with water (200 mL) in several portions and dried (35° C., 20 mbar, 20 hours). The dried crude product (22 g) is dissolved in toluene (250 mL) at 80-85° C. and aluminium oxide (Merck, 90 active basic; 10 g) is added. After stirring for 30 minutes at the stated temperature the mixture is filtered and the clear filtrate is concentrated in vacuo (40-50° C.) to a volume of 50 mL.

By cooling to 10° C. for 2 hours a colorless precipitate separates out which is filtered off over a suction filter, rinsed with toluene (10 mL) and dried (40° C., 20 mbar, 20 hours).

16 g (80% of theory) of the title compound 5-difluoromethoxy-2-[(3-methoxy-4-trideuteriomethoxy-2-pyridinyl)methylthio]-1H-benzimidazole are obtained as offwhite crystalline solid of m.p. 119-120° C.

Alternative Synthesis of Example 3

2.12 g of 2-chloromethyl-3-methoxy-4-trideuteriomethoxypyridinium chloride are added to a solution of 2.08 g of 2-mercapto-5-difluoromethoxy-1H-benzimidazole in 40 mL of ethanol and 20 mL of 1N sodium hydroxide solution, the mixture is stirred at 20° C. for 2 hours and then at 40° C. for a further hour. Ethanol is distilled off on a rotary evaporator (10 mbar/40° C.) and the colorless precipitate which thereby separates out is filtered off over a suction filter. It is rinsed with 1N sodium hydroxide solution and water and dried. After recrystallization from toluene according to example 3 the title compound is obtained as offwhite crystalline solid, yield 2.9 g; mp 118-120° C. Example 4

Synthesis of Starting Material
2-chloromethyl-3-methoxy-4-trideuteriomethoxy
pyridiniumchloride Preparation of
3-methoxy-2-methyl-4-trideuteriomethoxypyridine
N-oxide 4-chloro-3-methoxy-2-methylpyridine-N-oxide (10 g) and sodium trideuteriomethanolate (6.2 g) in deuteromethanol d4 (20 mL) were heated at reflux. After 15 hours the solvent was evaporated in vacuo, the residue was extracted with hot toluene (50 mL) and the insolubles were filtered off. Addition of diisopropylether to the filtrate precipitated a solid, which after drying in vacuo yielded 8.1 g of 3-methoxy-2-methyl-4-trisdeuteromethoxypyridine N-oxide as a light brown powder. It was subsequently used in the following step.

Preparation of 2-hydroxymethyl-3-methoxy-4-trideuteriomethoxypyridine

The product (8.1 g) from the previous step was dissolved in acetic anhydride (50 mL) and was heated at 90° C. for 2 hours. After evaporation in vacuo, the dark oily residue was agitated with 2N NaOH (20 mL) for 2 hours at 80° C. After cooling the product was extracted into dichloromethane, dried ($K_2CO_3$), and concentrated in vacuo to low volume. Addition of petroleum ether (50/70) afforded, after filtration and drying in vacuo 2-hydroxy-3-methoxy-4-trideuteriomethoxypyridine as light brown solid (5.5 g) which was used in the following step.

Preparation of
2-chloromethyl-3-methoxy-4-trideuteriomethoxy
pyridinium chloride The product form the previous step (5.5 g) was dissolved in dry dichloromethane (40 mL) and thionylchloride (3 mL) was added dropwise at 5-10° C. while stirring. The mixture was allowed to warm up to 20° C. and after 3 hours evaporated to dryness in vacuo.

Addition of toluene (20 mL) yielded 6.6 g of the title compound 2-chloromethyl-3-methoxy-4-trideuteriomethoxypyridinium chloride as light brown solid.

Material synthesized in this manner contained some difficult-to-remove impurities, which showed a propensity to get carried through the next steps leading to compounds of the present invention. For the preparation of compounds of the present invention with exceptionally high purity, it is therefore frequently preferable to resort to the deuterioalkoxylation method featured in Examples 3, 14 and 41.

Example 5

Synthesis of Sodium (S)-{[5-(difluoromethoxy)]-2-
[(3-methoxy-4-trideuteriomethoxy-2-pyridinyl)methylsulphinyl]-1H-benzimidazolide} hydrate 5.0 g of (S) {[5-(difluoromethoxy)]-2-[(3-methoxy-4-trideuteriomethoxy-2-pyridinyl)methylsulphinyl]-1H-benzimidazole} are suspended in 25 ml of isobutyl methyl ketone (MIBK) and 2.5 ml of 2-propanol and heated to an internal temperature of 45° C. The suspension is stirred at this temperature for 15 min. At 45° C., 1.25 g of 40% (w/w) aqueous sodium hydroxide solution and 02.5 ml of water are slowly added dropwise to this suspension. The solution is slowly cooled to room temperature. Between 45 and 30° C. crystallization, which can be accelerated by seeding, sets in. The resulting suspension is stirred at an internal temperature of <20° C. for another 18 h. The suspension is then filtered, and the crystals are washed with 2 ml of MIBK. Drying is carried out in a vacuum drying cabinet at <50 mbar and 35° C. The title compound is achieved as white to off white crystalline solid; yield 5.9 g, 99% of theory; the water content is between 12 to 14% corresponding to a trihydrate; m. p.: decomposition starts at 95° C., purity HPLC >99.7%, chiral HPLC >98.0% ee; $[\alpha]^{20}_D$=−89.0° (c=0.5, MeOH).

Example 6

Synthesis of Sodium (R/S)-{[5-(difluoromethoxy)]-
2-[(3-methoxy-4-trideuteriomethoxy-2-pyridinyl)
methylsulphinyl]-1H-benzimidazolide} hydrate 9.5 g of {[5-(difluoromethoxy)]-2-[(3-methoxy-4-trideuteriomethoxy-2-pyridinyl)methylsulphinyl]-1H-benzimidazole} are suspended in 57 ml of acetone and heated to an internal temperature of 45° C. The suspension is stirred at this temperature for 15 min. At 45° C., 2.4 g of 40% (w/w) aqueous sodium hydroxide solution is slowly added to this suspension. The solution is slowly cooled to room temperature. Between 30 and 25° C. crystallization, which can be accelerated by seeding, sets in. 4 ml of water is added. The resulting suspension is stirred at an internal temperature of <20° C. for 18 h. The suspension is then filtered, and the crystals are washed with 5 ml of acetone. Drying is carried out in a vacuum drying cabinet at <50 mbar and 40° C. The title compound is achieved as white to off white crystalline solid; yield 8.8 g, 88% of theory; The water content is 5.2%, by Karl Fischer titration, corresponding to a monohydrate; m.p.: 155-158° C. (decomposition), purity >99.3% by HPLC.

$^1$H-NMR (200 MHz, DMSO-d6): δ=3.78 (s, 3H), 4.34 (d, 12.9 Hz, 1H), 4.68 (d, 12.9 Hz, 1H), 6.72 (dd, 8.6 Hz, 2.4 Hz, 1H), 7.02 (t, 75.8 Hz, 1H), 7.07 (d, 5.6 Hz, 1H), 7.24 (d, 2.2 Hz, 1H), 7.44 (d, 8.6 Hz, 1H), 8.22 (d, 5.5 Hz, 1H); LC-MS: MNa$^+$=409, MH$^+$=387.

Example 7

Synthesis of Magnesium (S)-bis-{[5-(difluoromethoxy)]-2-[(3-methoxy-4-trideuteriomethoxy-2-pyridinyl)methylsulphinyl]-1H-benzimidazolide} hydrate 30. g of sodium (S)-{[5-(difluoromethoxy)]-2-[(3-methoxy-4-trideuteriomethoxy-2-pyridinyl)methylsulphinyl]-1H-benzimidazolide} (calculated as anhydrous substance) are suspended in 26 ml of water. The suspension is heated to 35-40° C. and stirred for another 10 min. This gives a clear solution. The clear solution is cooled to 22-27° C. 1.43 g of magnesium chloride hexahydrate are dissolved in 10 ml of water, and at room temperature and with stirring, this solution is slowly added dropwise to the sodium salt solution. The resulting suspension is then stirred at room temperature for another 18 h. The suspension is, filtered, and the product is washed twice with 10 ml of water. Drying in a vacuum drying cabinet at <50 mbar and 40-45° C. gives 2.2 g (74%) of the title compound of m. p.: decomposition starts at 169° C.; water content 6.4% by Karl Fischer titration, corresponding to a trihydrate; purity >99.7% HPLC, chiral HPLC >99.0% ee; $[\alpha]^{20}_D = -122°$ (c=0.5, MeOH).

Example 8

Synthesis of Magnesium (R/S)-bis-{[5-(difluoromethoxy)]-2-[(3-methoxy-4-trideuteriomethoxy-2-pyridinyl)methylsulphinyl]-1H-benzimidazolide} hydrate 3.0 g of sodium (R/S)-{[5-(difluoromethoxy)]-2-[(3-methoxy-4-trideuteriomethoxy-2-pyridinyl)methylsulphinyl]-1H-benzimidazolide} (calculated anhydrous substance) are suspended in 26 ml of water. The suspension is heated to 35-40° C. and stirred at 35-40° C. for another 10 min. This gives a clear solution. The clear solution is cooled to 22-27° C. 1.43 g of magnesium chloride hexahydrate are dissolved in 10 ml of water, and at room temperature and with stirring, this solution is slowly added dropwise to sodium salt solution. The resulting suspension is then stirred at room temperature for another 4 h. The suspension is filtered, and the product is washed twice with 15 ml of water. Drying in a vacuum drying cabinet at <50 mbar and 40-45° C. gives 2.1 g (70%) of the title compound of m.p. 179-181° C. (decomposition). Water content 4.7%, by Karl Fischer titration corresponding to a dihydrate, purity: 99.5% HPLC.

Example 9

4-Chloro-2-chloromethyl-3-methoxypyridinium chloride

At 85-95° C., a solution of 4-chloro-3-methoxy-2-methylpyridine-N-oxide (19.2 kg, 111 mol) in toluene (148 L), was added over 5-7 h to acetic anhydride (71 L). Under vacuum at about 60° C., the reaction mixture was concentrated until about 170 L had been distilled off. Toluene (160 L) was added and solvents were distilled off (160 L). This last operation was repeated once more. Then, toluene (14 L) and 40% aqueous NaOH (14.6 L) were added at 35-45° C. and the reaction mixture was kept at this temperature for 2-3 h. If at this point pH was below 13, more NaOH was added and heating continued for 2 more hours. The resulting biphasic reaction mixture was diluted with toluene (26 L) and saturated aqueous sodium bicarbonate (26 L), the phases were separated and the aqueous layer was extracted three times with toluene (26 L and 2×13 L). Finally, the combined organic phase was washed with saturated aqueous sodium bicarbonate (13 L) and concentrated under vacuum at 50-65° C. until about 115 L had been distilled off. After dilution with toluene (100 L), another 100 L of solvents were distilled off.

The resulting solution of 4-chloro-2-hydroxymethyl-3-methoxypyridine (~30% strength) was diluted with $CH_2Cl_2$ (48 L). DMF (65.5 g, 0.896 mol) was added in one portion and, then, thionyl chloride (11.1 kg, 93.2 mol) over 3-5 h at 15-30° C. After stirring for additional 1.5 h, about 45 L of solvents were distilled off. Toluene (20 L) was added and 20 L of solvents were again removed by distillation. Then, ethanol (1.5 L) was added to the resulting thick slurry. The solids were filtered off at 10-15° C., washed with toluene (17 L) and dried in vacuo at 30° C. to give 4-chloro-2-chloromethyl-3-methoxypyridinium chloride as an off-white solid (m. p. 132° C.); yield 15.0 kg (59%).

$^1$H-NMR (200 MHz, $CDCl_3$): δ=4.19 (s, 3H), 5.14 (s, 2H), 7.92 (d, 6.0 Hz, 1H), 8.59 (d, 6.0 Hz, 1H), 11.64 (br s, 1H); LC-MS: $MH^+$=192/194/196.

Example 10

4-Chloro-2-chloromethyl-3-trideuteriomethoxypyridinium chloride

Starting material, 4-chloro-2-methyl-3-trideuteriomethoxypyridine-N-oxide was prepared according to method D for the non-deuterated analogue in *J. Med. Chem.* 1992, 35, 1049-1057:

Starting from 3-hydroxy-2-methyl-4-pyrone, conversion with trideuterio-iodomethane in the presence of potassium carbonate in DMF yielded 2-methyl-3-trideuteriomethoxy-4-pyrone (yield: 83-96%), which upon heating with ammonia at 150° C. in ethanol gave, after crystallization from acetone/isopropanol 4:1; 4-hydroxy-2-methyl-trideuteriomethoxypyridine (yield: 52-60%). Treatment of this material with phosphorus oxychloride led to formation of 4-chloro-2-methyl-trideuteriomethoxypyridine (yield: 64-81%). Subsequent oxidation with hydrogen peroxide in acetic acid gave 4-chloro-2-methyl-3-trideuteriomethoxypyridine-N-oxide as a slightly yellow solid (yield: 87-89%).

The final transformations via 4-chloro-2-hydroxymethyl-3-trideuteriomethoxypyridine were carried out as described under Example 9 to give 4-chloro-2-chloromethyl-3-trideuteriomethoxypyridinium chloride as a colorless crystalline solid (m. p. 129-130° C.); yield 19.6 g (42%).

Example 11

2-Chloromethyl-3,4-bis(trideuteriomethoxy)pyridinium chloride

According to the procedure as described under Example 4 above, 4-chloro-2-methyl-3-trideuteriomethoxypyridine-N-oxide (25.3 g, 144 mmol; for preparation see Example 10) was converted into 2-methyl-3,4-bis(trideuteriomethoxy)pyridine-N-oxide (yield: 23.5 g, 96%), which, in turn, gave 2-hydroxymethyl-3,4-bis(trideuteriomethoxy)pyridine (yield: 13.0 g, 56%) and, ultimately, 2-chloromethyl-3,4-bis (trideuteriomethoxy)pyridinium chloride (yield: 15.4 g, 89%) as an off-white crystalline solid.

Example 12

5-Difluoromethoxy-2-[(4-chloro-3-methoxy-2-pyridinyl)methylthio]-1H-benzimidazole At 55-65° C., a solution of 4-chloro-2-chloromethyl-3-methoxypyridinium chloride (10.0 kg, 43.8 mol) in water (20 L) was added over 2-3 h to a mixture of 5-difluoromethoxy-1H-benzimidazole-2-thiol (8.84 kg, 40.9 mol), toluene (43 L), water (21 L) and 40% aqueous NaOH (10.3 kg, 103 mol). Stirring at 60° C. was continued for 2-3 h before the reaction mixture was cooled to 10-15° C. The precipitate was centrifuged off, washed with toluene (16 L) and re-pulped in water (122 L). Centrifugation followed by an aqueous rinse (32 L) and drying at 35° C. in vacuo gave 5-difluoromethoxy-2-[(4-chloro-3-methoxy-2-pyridinyl)methylthio]-1H-benzimidazole mono hydrate (KF=4.6%) as an off-white solid (m. p. 95-99° C.); yield 14.2 kg (92%).

$^1$H-NMR (200 MHz, DMSO-d6): δ=3.55 (br s, NH+H$_2$O), 3.92 (s, 3H), 4.79 (s, 2H), 6.97 (dd, 8.6 Hz, 2.3 Hz, 1H), 7.16 (t, 74.8 Hz, 1H), 7.28 (d, 2.2 Hz, 1H), 7.47 (d, 8.7 Hz, 1H), 7.55 (d, 5.3 Hz, 1H), 8.25 (d, 5.2 Hz, 1H); LC-MS: MH$^+$=372/374.

Example 13

5-Difluoromethoxy-2-[(4-chloro-3-trideuteriomethoxy-2-pyridinyl)methylthio]-1H-benzimidazole Starting from 4-chloro-2-chloromethyl-3-trideuteriomethoxypyridinium chloride (5.00 g, 21.6 mmol, Example 10) and following the procedure described under Example 12, 5-difluoromethoxy-2-[(4-chloro-3-trideuteriomethoxy-2-pyridinyl)methylthio]-1H-benzimidazole mono hydrate (KF=4.7%) was obtained as an off-white solid (m. p. 94-99° C.); yield 7.24 g (85%).

$^1$H-NMR (200 MHz, DMSO-d6): δ=4.79 (s, 2H), 6.98 (dd, 8.7 Hz, 2.3 Hz, 1H), 7.16 (t, 74.8 Hz, 1H), 7.28 (d, 2.0 Hz, 1H), 7.47 (d, 8.6 Hz, 1H), 7.55 (d, 5.2 Hz, 1H), 8.25 (d, 5.2 Hz, 1H), 12.75 (br s, 1H); LC-MS: MH$^+$=375/377.

Example 14

Alternative Process for 5-Difluoromethoxy-2-[(3-methoxy-4-trideuteriomethoxy-2-pyridinyl)methylthio]-1H-benzimidazole At 15-30° C., methanol-d4 (2.26 kg, 62.7 mol) was added over 30-60 min to a mixture of sodium tert-butoxide (6.00 kg, 62.4 mol) in DMAc (27 L). After heating to 57-65° C., a solution of 5-difluoromethoxy-2-[(4-chloro-3-methoxy-2-pyridinyl)methylthio]-1H-benzimidazole mono hydrate (6.08 kg, 15.6 mol) in DMAc (10 L) was added over 30-60 min. Stirring at 57-65° C. was continued for about 10 h. The reaction mixture was cooled to 20-30° C. and diluted with water (21 L) before the pH was adjusted to 7-8 with 20% aqueous HCl (~7.5 L). Precipitation of product was achieved by addition of water (75 h) over about 4 h. The resulting slurry was heated to 35-45° C. for 1.5 h before being chilled to 10-15° C. 5-difluoromethoxy-2-[(3-methoxy-4-trideuteriomethoxy-2-pyridinyl)methylthio]-1H-benzimidazole was obtained as a water-wet brownish solid by centrifugation including an aqueous rinse (58 L), re-pulping in water (78 L) and, again, centrifugation including another aqueous rinse (58 L); yield 10.4 kg, KF=49.7% (91%).

Drying of a sample of water-wet product (16.2 g, KF=49.7%) at 25° C. in vacuo gave an amorphous solid, which upon crystallization from toluene (30 mL) yielded water-free 5-difluoromethoxy-2-[(3-methoxy-4-trideuteriomethoxy-2-pyridinyl)methylthio]-1H-benzimidazole as an off-white solid (5.80 g, 71% recovery, m. p.=115-116° C.).

$^1$H-NMR (200 MHz, DMSO-d6): δ=3.82 (s, 3H), 4.68 (s, 2H), 6.97 (dd, 8.6 Hz, 2.1 Hz, 1H), 7.08 (d, 5.6 Hz, 1H), 7.16 (t, 74.8 Hz, 1H), 7.28 (br s, 1H), 7.47 (br d, ~8.3 Hz, 1H), 8.16 (d, 5.6 Hz, 1H), 12.75 (br s, 1H); LC-MS: MH$^+$=371.

Example 15

5-Difluoromethoxy-2-[(3-methoxy-4-dideuteriomethoxy-2-pyridinyl)methylthio]-1H-benzimidazole Starting from 5-difluoromethoxy-2-[(4-chloro-3-methoxy-2-pyridinyl)methylthio]-1H-benzimidazole mono hydrate (28.6 g, 73.4 mmol) and methanol-d2 (10.0 g, 294 mmol), the procedure described under Example 14 was followed to give 5-difluoromethoxy-2-[(3-methoxy-4-dideuteriomethoxy-2-pyridinyl)methylthio]-1H-benzimidazole as a water-wet brownish solid; yield 46.4 g, KF=51.6% (82%).

$^1$H-NMR (400 MHz, DMSO-d6): δ=3.81 (s, 3H), 3.86 (s, 1H), 4.67 (s, 2H), 6.97 (dd, 8.4 Hz, 2.0 Hz, 1H), 7.08 (d, 5.5 Hz, 1H), 7.16 (t, 74.7 Hz, 1H), 7.21-7.53 (br m, 2H), 8.16 (d, 5.5 Hz, 1H), 12.78 (br s, 1H); LC-MS: MH$^+$=370.

Example 16

5-Difluoromethoxy-2-[(3-methoxy-4-monodeuteriomethoxy-2-pyridinyl)methylthio]-1H-benzimidazole Starting from 5-difluoromethoxy-2-[(4-chloro-3-methoxy-2-pyridinyl)methylthio]-1H-benzimidazole mono hydrate (29.5 g, 75.6 mmol) and methanol-d1 (10.0 g, 303 mmol), the procedure described under Example 14 was followed to give 5-difluoromethoxy-2-[(3-methoxy-4-monodeuteriomethoxy-2-pyridinyl)methylthio]-1H-benzimidazole as a water-wet brownish solid; yield 50.3 g, KF=50.8% (89%).

$^1$H-NMR (200 MHz, DMSO-d6): δ=3.82 (s, 3H), 3.88 (s, 2H), 4.67 (s, 2H), 6.98 (dd, 8.6 Hz, 2.2 Hz, 1H), 7.08 (d, 5.6 Hz, 1H), 7.15 (t, 74.8 Hz, 1H), 7.22-7.53 (br m, 2H), 8.16 (d, 5.6 Hz, 1H), 12.79 (br s, 1H); LC-MS: MH$^+$=369.

Example 17

5-Difluoromethoxy-2-[(4-methoxy-3-trideuteriomethoxy-2-pyridinyl)methylthio]-1H-benzimidazole Starting from 5-difluoromethoxy-2-[(4-chloro-3-trideuteriomethoxy-2-pyridinyl)methylthio]-1H-benzimidazole mono hydrate (6.97 g, 17.7 mmol) and methanol (2.28 g, 71.2 mmol), the procedure described under Example 14 was followed to give 5-difluoromethoxy-2-[(4-methoxy-3-trideuteriomethoxy-2-pyridinyl)methylthio]-1H-benzimidazole as a water-wet brownish solid; yield 7.01 g, KF=19.1% (87%).

$^1$H-NMR (200 MHz, DMSO-d6): δ=3.89 (s, 3H), 4.68 (s, 2H), 6.97 (dd, 8.6 Hz, 2.0 Hz, 1H), 7.08 (d, 5.5 Hz, 1H), 7.16 (t, 74.7 Hz, 1H), 7.18-7.47 (br m, 2H), 8.16 (d, 5.6 Hz, 1H), 12.76 (br s, 1H); LC-MS: MH$^+$=371.

Example 18

5-Difluoromethoxy-2-[(3,4-bis(trideuteriomethoxy)-2-pyridinyl)methylthio]-1H-benzimidazole At 50-55° C., a 2-chloromethyl-3,4-bis(trideuteriomethoxy)pyridinium chloride (15.4 g, 66.8 mmol) was added portionwise over 30 min to a mixture of 5-difluoromethoxy-1H-benzimidazole-2-thiol (14.5 g, 66.8 mmol), ethanol (133 mL), and 2M aqueous NaOH (73.5 mL, 147 mmol). Stirring at 50-55° C. was continued for 1-2 h before ethanol was removed by distillation under vacuum at 40° C. The remaining aqueous emulsion was diluted with water (50 mL) and extracted three times with dichloromethane (165 mL portions). The combined organic phase was washed with 0.1M aqueous NaOH (165 mL), dried over $Na_2SO_4$, and evaporated to dryness to give 5-difluoromethoxy-2-[(3,4-bis(trideuteriomethoxy)-2-pyridinyl)methylthio]-1H-benzimidazole as a brown oil; yield 23.8 g (95%).

Example 19 rac-5-Difluoromethoxy-2-[(3-methoxy-4-trideuteriomethoxy-2-pyridinyl)methylsulfinyl]-1H-benzimidazole—large scale procedure At 25-35° C., aqueous sodium hypochlorite (10.5 kg at 10% strength, 14.2 mol) was added over 3-4 h to a solution of 5-difluoromethoxy-2-[(3-methoxy-4-trideuteriomethoxy-2-pyridinyl)methylthio]-1H-benzimidazole (10.4 kg, KF=49.7%, 14.2 mol) and 40% aqueous NaOH (2.84 kg) in a mixture of water (49 L) and isopropanol (49 L). Stirring at 25-35° C. was continued for 0.5-1 h before the reaction was quenched by addition of 1% aqueous $Na_2S_2O_3$ (4.3 L). Then, about 65 L of solvents were distilled off at 30-45° C. under vacuum. After dilution with water (55 L), another portion of solvents (8-10 L) was removed by distillation. While keeping the reaction mixture at 40-45° C., 10% aqueous acetic acid (~13 L) was added over 1.5 h until pH 8.5-9.5 was reached. Once crystallization had set in, the pH was slowly adjusted to 6.8-7.2 by addition of more 10% aqueous acetic acid (~0.6 L). After cooling to 20-25° C., crude product was filtered off and washed with water (7.5 L) and re-dissolved in a mixture of water (80 L), 40% aqueous NaOH (1.6 L) and $Na_2S_2O_3$ (60 g). The resulting slightly turbid aqueous solution was washed twice with MIBK (12 L each) and cleared by Hyflo treatment (0.40 kg), before the pH was adjusted to 9.0-9.5 by addition of 10% aqueous acetic acid (~8 L) at 40-45° C. Once product started to crystallize, further 10% acetic acid was added so as to continuously maintain a pH of 9.0-9.5. Finally, centrifugation at 20-25° C. including an aqueous rinse (7.5 L) and drying in vacuo at about 50° C. gave rac-5-difluoromethoxy-2-[(3-methoxy-4-trideuteriomethoxy-2-pyridinyl)methylsulfinyl]-1H-benzimidazole as an off-white solid (m. p.=134-135° C., decomp.); yield 3.59 kg (65%).

$^1$H-NMR (400 MHz, DMSO-d6): δ=3.78 (s, 3H), 4.67 (d, 13.1 Hz, 1H), 4.73 (d, 13.1 Hz, 1H), 7.10 (d, 5.5 Hz, 1H), 7.18 (br d, 8.7 Hz, 1H), 7.24 (t, 74.4 Hz, 1H), 7.44 (br s, 1H), 7.70 (br s, 1H), 8.15 (d, 5.5 Hz, 1H), 13.73 (br s, 1H); LC-MS: $MH^+$=387.

Example 20 rac-5-Difluoromethoxy-2-[(3-methoxy-4-dideuteriomethoxy-2-pyridinyl)methylsulfinyl]-1H-benzimidazole Starting from wet 5-difluoromethoxy-2-[(3-methoxy-4-dideuteriomethoxy-2-pyridinyl)methylthio]-1H-benzimidazole (32.7 g, KF=51.6%, 42.8 mmol) and following the procedure described under Example 19, rac-5-difluoromethoxy-2-[(3-methoxy-4-dideuteriomethoxy-2-pyridinyl)methylsulfinyl]-1H-benzimidazole was obtained as an off-white solid (m. p.=133-135° C., decomp.); yield 10.8 g (65%).

$^1$H-NMR (200 MHz, DMSO-d6): δ=3.32 (br s, NH+$H_2O$), 3.77 (s, 3H), 3.86 (s, 1H), 4.65 (d, 13.1 Hz, 1H), 4.73 (d, 13.1 Hz, 1H), 7.10 (d, 5.5 Hz, 1H), 7.15 (dd, 8.8 Hz, 2.4 Hz, 1H), 7.23 (t, 74.4 Hz, 1H), 7.44 (d, 2.2 Hz, 1H), 7.69 (d, 8.8 Hz, 1H), 8.15 (d, 5.5 Hz, 1H); LC-MS: $MH^+$=386.

Example 21 rac-5-Difluoromethoxy-2-[(3-methoxy-4-monodeuteromethoxy-2-pyridinyl)methylsulfinyl]-1H-benzimidazole Starting from wet 5-difluoromethoxy-2-[(3-methoxy-4-monodeuteriomethoxy-2-pyridinyl)methylthio]-1H-benzimidazole (34.8 g, KF=50.8%, 46.5 mmol) and following the procedure described under Example 19, rac-5-difluoromethoxy-2-[(3-methoxy-4-monodeuteriomethoxy-2-pyridinyl)methylsulfinyl]-1H-benzimidazole was obtained as an off-white solid (m. p.=134-135° C., decomp.); yield 14.0 g (78%).

$^1$H-NMR (200 MHz, DMSO-d6): δ=3.78 (s, 3H), 3.88 (s, 2H), 4.66 (d, 13.2 Hz, 1H), 4.73 (d, 13.1 Hz, 1H), 7.10 (d, 5.6 Hz, 1H), 7.16 (dd, 8.8 Hz, 2.4 Hz, 1H), 7.24 (t, 74.4 Hz, 1H), 7.45 (d, 2.2 Hz, 1H), 7.69 (d, 8.8 Hz, 1H), 8.15 (d, 5.5 Hz, 1H), 13.77 (br s, 1H); LC-MS: $MH^+$=385.

Example 22 rac-5-Difluoromethoxy-2-[(4-methoxy-3-trideuteriomethoxy-2-pyridinyl)methylsulfinyl]-1H-benzimidazole Starting from wet 5-difluoromethoxy-2-[(4-methoxy-3-trideuteriomethoxy-2-pyridinyl)methylthio]-1H-benzimidazole (3.00 g, KF=19.1%, 6.55 mmol) and following the procedure described under Example 23 or 44, rac-5-difluoromethoxy-2-[(4-methoxy-3-trideuteriomethoxy-2-pyridinyl)methylsulfinyl]-1H-benzimidazole was obtained, after crystallization from TBME (10 mL); as an off-white solid (m. p.=133-134° C., decomp.); yield 1.83 g (72%).

$^1$H-NMR (200 MHz, DMSO-d6): δ=3.90 (s, 3H), 4.66 (d, 13.1 Hz, 1H), 4.73 (d, 13.1 Hz, 1H), 7.10 (d, 5.6 Hz, 1H), 7.15 (dd, 8.9 Hz, 2.4 Hz, 1H), 7.24 (t, 74.4 Hz, 1H), 7.45 (d, 2.1 Hz, 1H), 7.69 (d, 8.8 Hz, 1H), 8.15 (d, 5.5 Hz, 1H), 13.77 (br s, 1H); LC-MS: $MH^+$=387.

Example 23 rac-5-Difluoromethoxy-2-[(3,4-bis(trideuteriomethoxy)-2-pyridinyl)methylsulfinyl]-1H-benzimidazole 5-Difluoromethoxy-2-[(3,4-bis(trideuteriomethoxy)-2-pyridinyl)methylthio]-1H-benzimidazole (23.8 g, 63.7 mmol) was dissolved in $CH_2Cl_2$ (210 mL) and cooled to −55 to −40° C. At this temperature, a solution of 3-chloroperoxybenzoic acid (wet, 77% strength, 15.8 g, 70.5 mmol) in $CH_2Cl_2$ (110 mL) was slowly added over 1.5 h. After one more h at −55 to −40° C., triethylamine (12.3 mL, 88.5 mmol) and a 1:1 mixture of 6% aqueous $Na_2CO_3$ and 2% aqueous $Na_2S_2O_3$ (140 mL) were successively added while allowing the mixture to warm to about 0° C. Stirring was continued for 1 h at ambient temperature. The phases were separated, and the organic layer was washed twice with a 1:1 mixture of 6% aqueous $Na_2CO_3$ and 2% aqueous $Na_2S_2O_3$ and once with water (140 mL each) before being evaporated to dryness. After crystallization from diisopropyl ether (700 mL), rac-5-difluoromethoxy-2-[(3,4-bis(trideuteriomethoxy)-2-pyridinyl)methylsulfinyl]-1H-benzimidazole was obtained as an off-white solid; yield 20.9 g (84%).

Example 24 rac-5-Difluoromethoxy-2-[(3-methoxy-4-dideuteriomethoxy-2-pyridinyl)methylsulfinyl]-1H-benzimidazole sodium salt mono hydrate Starting from rac-5-difluoromethoxy-2-[(3-methoxy-4-dideuteriomethoxy-2-pyridinyl)methylsulfinyl]-1H-benzimidazole (8.10 g, 21.0 mmol), the procedure described under Example 6 gave rac-5-difluoromethoxy-2-[(3-methoxy-4-dideuteriomethoxy-2-pyridinyl)methylsulfinyl]-1H-benzimidazole sodium salt mono hydrate as an off-white solid (m. p.=150-152° C. (decomp.), KF=4.8%); yield 6.05 g (68%).

$^1$H-NMR (200 MHz, DMSO-d6): δ=3.77 (s, 3H), 3.85 (s, 1H), 4.36 (d, 12.9 Hz, 1H), 4.66 (d, 12.9 Hz, 1H), 6.73 (dd, 8.6 Hz, 2.4 Hz, 1H), 7.02 (t, 75.8 Hz, 1H), 7.07 (d, 5.6 Hz, 1H), 7.25 (d, 2.3 Hz, 1H), 7.45 (d, 8.6 Hz, 1H), 8.22 (d, 5.5 Hz, 1H); LC-MS: MNa$^+$=408, MH$^+$=386.

Example 25 rac-5-Difluoromethoxy-2-[(3-methoxy-4-monodeuteriomethoxy-2-pyridinyl)methylsulfinyl]-1H-benzimidazole sodium salt mono hydrate Starting from rac-5-difluoromethoxy-2-[(3-methoxy-4-monodeuteriomethoxy-2-pyridinyl)methylsulfinyl]-1H-benzimidazole (10.2 g, 26.5 mmol), the procedure described under Example 6 gave rac-5-difluoromethoxy-2-[(3-methoxy-4-monodeuteriomethoxy-2-pyridinyl)methylsulfinyl]-1H-benzimidazole sodium salt mono hydrate as an off-white solid (m. p.=151-152° C. (decomp.), KF=4.1%); yield 8.95 g (79%).

$^1$H-NMR (200 MHz, DMSO-d6): δ=3.78 (s, 3H), 3.88 (s, 2H), 4.34 (d, 12.9 Hz, 1H), 4.68 (d, 12.9 Hz, 1H), 6.73 (dd, 8.6 Hz, 2.4 Hz, 1H), 7.03 (t, 75.8 Hz, 1H), 7.08 (d, 5.5 Hz, 1H), 7.24 (d, 2.2 Hz, 1H), 7.44 (d, 8.6 Hz, 1H), 8.22 (d, 5.5 Hz, 1H); LC-MS: MNa$^+$=407, MH$^+$=385.

Example 26 rac-5-Difluoromethoxy-2-[(3,4-bis(trideuteriomethoxy)-2-pyridinyl)methylsulfinyl]-1H-benzimidazole sodium salt mono hydrate At 15-25° C., 6M aqueous NaOH (8.92 mL, 53.5 mmol) was added over about 15 min to a solution of rac-5-difluoromethoxy-2-[(3,4-bis(trideuteriomethoxy)-2-pyridinyl)methylsulfinyl]-1H-benzimidazole (21.0 g, 53.9 mmol) in a 6:1 mixture of ethanol/dichloromethane (725 mL). After stirring for another 10 min at room temperature, most of the solvents were distilled off. The resulting concentrate (115 g) was diluted with diisopropyl ether (1.7 L). Some dark waxy residue remained undissolved, and the supernatant clear yellow solution was decanted off. To this solution, another portion of diisopropyl ether (3.4 L) was added to effect precipitation of product. The suspension was cooled to 0° C., and the solids were filtered off, washed with diisopropyl ether (100 mL) and dried at 40° C. in vacuo to give rac-5-Difluoromethoxy-2-[(3,4-bis(trideuteriomethoxy)-2-pyridinyl)methylsulfinyl]-1H-benzimidazole sodium salt mono hydrate as an off-white solid (KF=4.0%); yield 18.9 g (82%).

$^1$H-NMR (400 MHz, DMSO-d6): δ=4.32 (d, 12.9 Hz, 1H), 4.70 (d, 12.9 Hz, 1H), 6.72 (dd, 8.6 Hz, 2.4 Hz, 1H), 7.04 (t, 75.8 Hz, 1H), 7.08 (d, 5.5 Hz, 1H), 7.23 (d, 2.4 Hz, 1H), 7.44 (d, 8.6 Hz, 1H), 8.22 (d, 5.5 Hz, 1H); LC-MS: MNa$^+$=412, MH$^+$=390.

Example 27 rac-5-Difluoromethoxy-2-[(3-methoxy-4-trideuteriomethoxy-2-pyridinyl)methylsulfinyl]-1H-benzimidazole sodium salt sesqui hydrate At 48-55° C., rac-5-difluoromethoxy-2-[(3-methoxy-4-trideuteriomethoxy-2-pyridinyl)methylsulfinyl]-1H-benzimidazole sodium salt mono hydrate (2.93 kg, 6.87 mol) was dissolved in a mixture of isopropanol (12 L) and water (0.50 L). After treatment with Hyflo Super Cel (56 g) and cooling to 18-25° C., crystallization was accomplished by seeding with an authentic sample of product followed by stirring for 40 h at 18-25° C. and another 5 h at 10-15° C. Centrifugation and drying at 45° C. in vacuo gave rac-5-difluoromethoxy-2-[(3-methoxy-4-trideuteriomethoxy-2-pyridinyl)methylsulfinyl]-1H-benzimidazole sodium salt sesqui hydrate as a white solid (m. p.=140-142° C. (decomp.), KF=6.6%); yield 2.28 kg (78%).

Example 28

(S)-5-Difluoromethoxy-2-[(3-methoxy-4-trideuteriomethoxy-2-pyridinyl)methylsulfinyl]-1H-benzimidazole—large scale procedure for undried starting material At room temperature, 382 g of wet 5-difluoromethoxy-2-[(3-methoxy-4-trideuteriomethoxy-2-pyridinyl)methylthio]-1H-benzimidazole (KF=47.6%, 0.540 mol) were suspended in 2.44 L of methyl isobutyl ketone together with (+)-L-tartaric acid bis-(N-pyrrolidinamide) (55.0 g). The mixture was heated to 40° C. and about 1.25 L of solvent were evaporated under vacuum to remove water. Then, zirconium (IV) n-propoxide (24.0 mL, 70% in n-propanol) was added and stirring at 40° C. was continued for one more hour. After cooling to 30° C., N-ethyldiisopropylamine (6.5 mL) and cumene hydroperoxide (103 mL, ~80% strength) were added. After stirring for about 18 h at 30° C., TLC indicated no further conversion of starting material. The clear reaction mixture was diluted with 500 mL of methyl isobutyl ketone and quenched with 7.0 g of sodium thiosulphate in 800 mL of saturated sodium bicarbonate solution. After phase separation, the organic layer was washed twice with 400 mL of saturated sodium bicarbonate solution. To the organic phase, 1.5 L of water were added, and the pH was adjusted to pH=13 using 40% aqueous sodium hydroxide. The organic layer was extracted with another 400 mL of water at pH 13. After treatment with Hyflo Super Cel (5.0 g), the pH of the combined aqueous phase is adjusted to about 9 by addition of 10% aqueous acetic acid at 40-45° C. Once precipitation of product had set in, the mixture was stirred for another 12 h with eventual readjustment of the pH. Crude product (160 g, 75% yield) with an optical purity of >98% was obtained by filtration including an aqueous rinse (200 mL). To further increase the purity, crude product was dissolved in dichloromethane (2.0 L) and washed with water (400 mL). Crystallization was achieved by a solvent chase with TBME (final volume about 1.1 L). The crystals were filtered off at about 0° C., washed with TBME (400 mL), and dried at 30° C. in vacuo to give (S)-5-difluoromethoxy-2-[(3-methoxy-4-trideuteriomethoxy-2-pyridinyl)methylsulfinyl]-1H-benzimidazole as an off-white solid (m. p. 146-148° C. (decomp.); KF=0.80%); yield 135 g (64%).

Chiral HPLC: >98.0% ee; optical rotation: $[\alpha]_D=-98°$ (MeOH, c=0.50).

$^1$H-NMR (200 MHz, DMSO-d6): δ=3.41 (br s, NH+H$_2$O), 3.77 (s, 3H), 4.65 (d, 13.0 Hz, 1H), 4.73 (d, 13.1 Hz, 1H), 7.09 (d, 5.6 Hz, 1H), 7.15 (dd, 8.9 Hz, 2.4 Hz, 1H), 7.23 (t, 74.4 Hz, 1H), 7.44 (d, 2.1 Hz, 1H), 7.68 (d, 8.9 Hz, 1H), 8.14 (d, 5.5 Hz, 1H); LC-MS: MH$^+$=387.

Example 29

(R)-5-Difluoromethoxy-2-[(3-methoxy-4-trideuteriomethoxy-2-pyridinyl)methylsulfinyl]-1H-benzimidazole Starting from 5-difluoromethoxy-2-[(3-methoxy-4-trideuteriomethoxy-2-pyridinyl)methylthio]-1H-benzimidazole (70.7 g, KF=47.6%, 100 mmol) and using (−)-D-tartaric acid bis-(N-pyrrolidinamide) (10.3 g, 40.0 mmol) as chiral ligand, the procedure described under Example 28 gave, after recrystallization from TBME, (R)-5-difluoromethoxy-2-[(3-methoxy-4-trideuteriomethoxy-2-pyridinyl)methylsulfinyl]-1H-benzimidazole as an off-white solid (m. p. 140-142° C. (decomp.); KF=0.8%); yield 22.2 g (57%).

Chiral HPLC: >98.0% ee; optical rotation: $[\alpha]_D=+970$ (MeOH, c=0.50).

$^1$H-NMR (200 MHz, DMSO-d6): δ=3.77 (s, 3H), 4.65 (d, 13.2 Hz, 1H), 4.73 (d, 13.1 Hz, 1H), 7.09 (d, 5.5 Hz, 1H), 7.16 (br d, ~10.3 Hz, 1H), 7.23 (t, 74.4 Hz, 1H), 7.44 (br s, 1H), 7.68 (br s, 1H), 8.14 (d, 5.5 Hz, 1H), 13.73 (br s, 1H); LC-MS: MH$^+$=387.

Example 30

(R)-5-Difluoromethoxy-2-[(3-methoxy-4-trideuteriomethoxy-2-pyridinyl)methylsulfinyl]-1H-benzimidazole sodium salt trihydrate Starting from (R)-5-difluoromethoxy-2-[(3-methoxy-4-trideuteriomethoxy-2-pyridinyl)methylsulfinyl]-1H-benzimidazole (15.5 g, 40.1 mmol) and following the procedure described under Example 5, (R)-5-difluoromethoxy-2-[(3-methoxy-4-trideuteriomethoxy-2-pyridinyl)methylsulfinyl]-1H-benzimidazole sodium salt trihydrate was obtained as a white solid (m. p. 98-103° C. (decomp.); KF=11.3%); yield 17.4 g (94%).

Chiral HPLC: >98.0% ee; optical rotation: $[\alpha]_D=+91°$ (MeOH, c=0.50).

Example 31

Bis-[(R)-5-Difluoromethoxy-2-[(3-methoxy-4-trideuteriomethoxy-2-pyridinyl)methylsulfinyl]-1H-benzimidazole] magnesium salt trihydrate Starting from (R)-5-difluoromethoxy-2-[(3-methoxy-4-trideuteriomethoxy-2-pyridinyl)methylsulfinyl]-1H-benzimidazole sodium salt (2.30 g, KF=11.3%, 5.00 mmol) and following the procedure described under Example 7, bis-[(R)-5-difluoromethoxy-2-[(3-methoxy-4-trideuteriomethoxy-2-pyridinyl)methylsulfinyl]-1H-benzimidazole] magnesium salt trihydrate was obtained as a white solid (m. p. 141-145° C. (decomp.); KF=6.9%); yield 1.23 g (58%).

Chiral HPLC: >99.0% ee; optical rotation: $[\alpha]_D=+120°$ (MeOH, c=0.50).

Example 32 rac-5-Difluoromethoxy-2-[(3-methoxy-4-trideuteriomethoxy-2-pyridinyl)methylsulfinyl]-1H-benzimidazole sodium salt mono hydrate At 15-30° C., 40% aqueous NaOH (0.85 kg, 8.50 mol) was added over 10-30 min to a solution of rac-5-difluoromethoxy-2-[(3-methoxy-4-trideuteriomethoxy-2-pyridinyl)methylsulfinyl]-1H-benzimidazole (3.29 kg, 8.51 mol) in acetone (18 L). The resulting suspension was heated at 50-55° C. until a clear solution was obtained. Crystallization of product was achieved by slow cooling to 10-15° C. over about 12 h. The solids were filtered off and washed with acetone (1.7 L) before being re-crystallized from acetone/water 32:1 (19 L). Finally, drying at 50° C. in vacuo gave rac-5-difluoromethoxy-2-[(3-methoxy-4-trideuteriomethoxy-2-pyridinyl)methylsulfinyl]-1H-benzimidazole sodium salt mono hydrate as an off-white solid (m. p.=151-152° C. (decomp.), KF=4.3%); yield 2.93 kg (81%).

$^1$H-NMR (200 MHz, DMSO-d6): δ=3.78 (s, 3H), 4.34 (d, 12.9 Hz, 1H), 4.68 (d, 12.9 Hz, 1H), 6.72 (dd, 8.6 Hz, 2.4 Hz, 1H), 7.02 (t, 75.8 Hz, 1H), 7.07 (d, 5.6 Hz, 1H), 7.24 (d, 2.2 Hz, 1H), 7.44 (d, 8.6 Hz, 1H), 8.22 (d, 5.5 Hz, 1H); LC-MS: MNa$^+$=409, MH$^+$=387.

Example 33 rac-5-Difluoromethoxy-2-[(3-methoxy-4-dideuteriomethoxy-2-pyridinyl)methylsulfinyl]-1H-benzimidazole sodium salt mono hydrate Starting from rac-5-difluoromethoxy-2-[(3-methoxy-4-dideuteriomethoxy-2-pyridinyl)methylsulfinyl]-1H-benzimidazole (8.10 g, 21.0 mmol), the procedure described under Example 32 gave rac-5-difluoromethoxy-2-[(3-methoxy-4-dideuteriomethoxy-2-pyridinyl)methylsulfinyl]-1H-benzimidazole sodium salt mono hydrate as an off-white solid (m. p.=150-152° C. (decomp.), KF=4.8%); yield 6.05 g (68%).

$^1$H-NMR (200 MHz, DMSO-d6): δ=3.77 (s, 3H), 3.85 (s, 1H), 4.36 (d, 12.9 Hz, 1H), 4.66 (d, 12.9 Hz, 1H), 6.73 (dd, 8.6 Hz, 2.4 Hz, 1H), 7.02 (t, 75.8 Hz, 1H), 7.07 (d, 5.6 Hz, 1H), 7.25 (d, 2.3 Hz, 1H), 7.45 (d, 8.6 Hz, 1H), 8.22 (d, 5.5 Hz, 1H); LC-MS: MNa$^+$=408, MH$^+$=386.

Example 34 rac-5-Difluoromethoxy-2-[(3-methoxy-4-monodeuteriomethoxy-2-pyridinyl)methylsulfinyl]-1H-benzimidazole sodium salt mono hydrate Starting from rac-5-difluoromethoxy-2-[(3-methoxy-4-monodeuteriomethoxy-2-pyridinyl)methylsulfinyl]-1H-benzimidazole (10.2 g, 26.5 mmol), the procedure described under Example 32 gave rac-5-difluoromethoxy-2-[(3-methoxy-4-monodeuteriomethoxy-2-pyridinyl)methylsulfinyl]-1H-benzimidazole sodium salt mono hydrate as an off-white solid (m. p.=151-152° C. (decomp.), KF=4.1%); yield 8.95 g (79%).

$^1$H-NMR (200 MHz, DMSO-d6): δ=3.78 (s, 3H), 3.88 (s, 2H), 4.34 (d, 12.9 Hz, 1H), 4.68 (d, 12.9 Hz, 1H), 6.73 (dd, 8.6

Hz, 2.4 Hz, 1H), 7.03 (t, 75.8 Hz, 1H), 7.08 (d, 5.5 Hz, 1H), 7.24 (d, 2.2 Hz, 1H), 7.44 (d, 8.6 Hz, 1H), 8.22 (d, 5.5 Hz, 1H); LC-MS: MNa$^+$=407, MH$^+$=385.

Example 35

Bis-[rac-5-Difluoromethoxy-2-[(3-methoxy-4-trideuteriomethoxy-2-pyridinyl)methylsulfinyl]-1H-benzimidazole] magnesium salt di hydrate At 40° C., a solution of rac-5-difluoromethoxy-2-[(3-methoxy-4-trideuteriomethoxy-2-pyridinyl)methylsulfinyl]-1H-benzimidazole sodium salt (500 mg, KF=4.3%, 1.17 mmol) in water (10.0 mL) was subjected to a clean filtration. After cooling to room temperature, a solution of anhydrous magnesium chloride (61.4 mg, 0.644 mmol) in 1.0 mL of water was added. The resulting suspension was stirred at room temperature for an additional 18 h before being cooled to 0° C. and filtered. The filter cake was re-pulped in water (7.5 mL), filtered, rinsed with water (5.0 mL) and dried at 40° C. in vacuo to give bis-[rac-5-difluoromethoxy-2-[(3-methoxy-4-trideuteriomethoxy-2-pyridinyl)methylsulfinyl]-1H-benzimidazole] magnesium salt di hydrate as a white solid (m. p. 180-182° C. (decomp.); KF=4.7%; HPLC: 99.5% a/a); yield 369 mg (76%).

Example 36

(S)-5-Difluoromethoxy-2-[(3-methoxy-4-trideuteriomethoxy-2-pyridinyl)methylsulfinyl]-1H-benzimidazole sodium salt At room temperature, to a suspension of (S)-5-difluoromethoxy-2-[(3-methoxy-4-trideuteriomethoxy-2-pyridinyl)methylsulfinyl]-1H-benzimidazole (100 g, 0.259 mol) in a mixture of methyl isobutyl ketone (750 mL), isopropanol (75 mL), and water (5.0 mL) was added 40% aqueous NaOH (18.1 mL, 259 mmol). After heating to 50° C. a clear solution was obtained, which was subjected to treatment with Hyflo Super Cel (10.0 g). Crystallization of product set in upon cooling to room temperature and was driven to completion by further cooling to 0° C. Finally, the crystals were filtered off, washed with methyl isobutyl ketone (3 portions, 40 mL each) and dried at 35° C. in vacuo to give (S)-5-difluoromethoxy-2-[(3-methoxy-4-trideuteriomethoxy-2-pyridinyl)methylsulfinyl]-1H-benzimidazole sodium salt as a white hygroscopic solid (m. p. 105-106° C. (decomp.); KF=10.3%); yield 105 g (89%).

Chiral HPLC: >99.0% ee; optical rotation: $[\alpha]_D$=−94° (MeOH, c=0.50).

Example 37

(R)-5-Difluoromethoxy-2-[(3-methoxy-4-trideuteriomethoxy-2-pyridinyl)methylsulfinyl]-1H-benzimidazole sodium salt Starting from (R)-5-difluoromethoxy-2-[(3-methoxy-4-trideuteriomethoxy-2-pyridinyl)methylsulfinyl]-1H-benzimidazole (15.5 g, 40.1 mmol) and following the procedure described under Example 36, (R)-5-difluoromethoxy-2-[(3-methoxy-4-trideuteriomethoxy-2-pyridinyl)methylsulfinyl]-1H-benzimidazole sodium salt was obtained as a white hygroscopic solid (m. p. 98-103° C. (decomp.); KF=11.3%); yield 17.4 g (94%).

Chiral HPLC: >98.0% ee; optical rotation: $[\alpha]_D$=+91° (MeOH, c=0.50).

Example 38

Bis-[(S)-5-Difluoromethoxy-2-[(3-methoxy-4-trideuteriomethoxy-2-pyridinyl)methylsulfinyl]-1H-benzimidazole] magnesium salt tri hydrate Starting from (S)-5-difluoromethoxy-2-[(3-methoxy-4-trideuteriomethoxy-2-pyridinyl)methylsulfinyl]-1H-benzimidazole sodium salt (500 mg, KF=10.3%, 1.10 mmol) and following the procedure described under Example 35, bis-[(S)-5-difluoromethoxy-2-[(3-methoxy-4-trideuteriomethoxy-2-pyridinyl)methylsulfinyl]-1H-benzimidazole] magnesium salt tri hydrate was obtained as a white solid (m. p. 169-175° C. (decomp.); KF=6.4%); yield 350 mg (75%).

Chiral HPLC: >99.0% ee; optical rotation: $[\alpha]_D$=−122° (MeOH, c=0.50).

Example 39

Synthesis of Starting Material 5-trideuteriomethoxy-1H-benzimidazole-2-thiol

Preparation of 4-trideuteriomethoxy-nitrobenzene

To a solution of sodium hydroxide (15.6 g, 390 mmol) in a mixture of methanol-d4 (47.4 mL, 1.17 mol) and THF (50 mL) was added a solution of 1-fluoro-4-nitrobenzene (50.0 g, 354 mmol) in THF (200 mL) over 2 h at 15-25° C. The resulting suspension was stirred for 3 more h at room temperature before 10% aqueous HCl (100 mL) and toluene (150 mL) were added. The organic phase was separated and evaporated to dryness to give 4-trideuteriomethoxy-nitrobenzene as a brown oil, which crystallized upon standing (m. p. 48-51° C.); yield 56.6 g (quantitative).

$^1$H-NMR (200 MHz, DMSO-d6): δ=7.15 (m, 2H), 8.22 (m, 2H); GC-MS: M$^+$=156.

Preparation of 4-trideuteriomethoxy-acetanilide

An autoclave was charged with 10% Pd/C (3.6 g, water wet), 4-trideuteriomethoxy-nitrobenzene (72.5 g, 464 mmol) and isopropanol (508 mL). After thorough purging with nitrogen (4 times), the resulting mixture was stirred under hydrogen pressure (3-4 bar) at 50-60° C. until the uptake of hydrogen stopped (about 2.5 h). The reaction mixture was cooled to room temperature and acetic anhydride (62.5 mL, 580 mmol) was added. Stirring was continued for 4 more h before the catalyst was filtered off and washed with hot 2-propanol (270 mL, about 60° C.). The combined filtrates were concentrated under vacuum to about 150 mL, methylcyclohexane (350 mL) was added, and the resulting slurry was cooled to 10° C. Filtration and drying at 45° C. in vacuo gave 4-trideuteriomethoxy-acetanilide as a grayish solid (m. p. 125-127° C.); yield 67.0 g (86%).

$^1$H-NMR (200 MHz, DMSO-d6): δ=2.00 (s, 3H), 6.85 (m, 2H), 7.47 (m, 2H), 9.74 (br s, 1H); LC-MS: MH$^+$=169.

Preparation of 2-nitro-4-trideuteriomethoxy-aniline

At 10-15° C., 50% aqueous nitric acid (63.0 mL, 654 mmol) was added over 1.5 h to a solution of 4-trideuteriomethoxy-acetanilide (50.0 g, 297 mmol) in acetic acid (175 mL). Stirring was continued for 18 h at room temperature. Then, 20% aqueous NaOH (671 mL) was added over about 1 h at 15-20° C. The resulting brown suspension was heated at 50° C. for 20 h before the pH was adjusted to about 8 by addition of 20% aqueous HCl (49 mL). Crude product was obtained by cooling to 10° C. and filtration. After an aqueous rinse, the filter cake was slurried at 60° C. in isopropanol (200 mL) and water (300 mL) was added over 1 h. While maintaining the temperature between 50 and 60° C., 190 mL of solvents were distilled off. The resulting suspension was cooled to 10° C., filtered and washed with water (60 mL) to provide after drying at 30° C. in vacuo 2-nitro-4-trideuteriomethoxy-aniline as a red solid (m. p. 120-122° C.); yield 46.7 g (92%).

$^1$H-NMR (200 MHz, DMSO-d6): δ=7.00 (d, 9.3 Hz, 1H), 7.16 (dd, 9.3 Hz, 2.9 Hz, 1H), 7.24 (br s, 2H), 7.37 (d, 2.9 Hz, 1H); GC-MS: M$^+$=171.

Preparation of
5-trideuteriomethoxy-1H-benzimidazole-2-thiol

An autoclave was charged with 10% Pd/C (2.23 g, water wet), 2-nitro-4-trideuteriomethoxy-acetanilide (45.6 g, 267 mmol) and isopropanol (460 mL). After thorough purging with nitrogen (4 times), the resulting mixture was stirred under hydrogen pressure (3-4 bar) at 40-50° C. until the uptake of hydrogen stopped (about 6 h). Then, O-ethylxanthic acid potassium salt (51.2 g, 319 mmol) was added and the reaction mixture was heated at reflux for 23 h. Water (340 mL) was added and the pH was adjusted to 12.5 with 20% aqueous NaOH (10 mL) before roughly the amount of isopropanol (460 mL) was distilled off. The resulting dark suspension was treated with charcoal (10 g), cleared by filtration and washed with toluene (350 mL). Product was precipitated by addition of 20% aqueous HCl (53 mL) and isolated by filtration at 0° C. Rinsing with water (100 mL) and drying at 35° C. in vacuo finally gave 5-trideuteriomethoxy-1H-benzimidazole-2-thiol as an off-white solid (m. p. 247-250° C.); yield 45.5 g (93

$^1$H-NMR (400 MHz, DMSO-d6): δ=6.67 (d, 2.3 Hz, 1H), 6.72 (dd, 8.7 Hz, 2.4 Hz, 1H), 7.03 (d, 8.6 Hz, 1H), 12.36 (br s, 1H), 12.40 (br s, 1H); LC-MS: MH$^+$=184.

Example 40

Synthesis of Starting Material
4-chloro-2-chloromethyl-3,5-dimethylpyridinium chloride Preparation of
4-chloro-2-hydroxymethyl-3,5-dimethylpyridine At 90-95° C., a solution of 4-chloro-2,3,5-trimethylpyridine-N-oxide (60.0 g, 350 mmol) in toluene (920 mL), which was kept at about 60° C., was added over 7 h to acetic anhydride (232 mL). Under vacuum at about 60° C., the reaction mixture was concentrated until 820 mL had been distilled off. Toluene (840 mL) was added and, again, solvents were distilled off (940 mL). Then, toluene (180 mL) and 40% aqueous NaOH (80 mL) were added before the reaction mixture was heated at 50° C. for about 15 h. After addition of saturated aqueous sodium bicarbonate (120 mL), the phases were separated and the aqueous layer was extracted once more with toluene (80 mL). Finally, the combined organic phase was washed with saturated aqueous sodium bicarbonate (120 mL) and evaporated to dryness to give 4-chloro-2-hydroxymethyl-3,5-dimethylpyridine as a brownish oil which solidified upon standing; yield 61.8 g (quantitative).

$^1$H-NMR (200 MHz, DMSO-d6): δ=2.30 (s, 3H), 2.36 (s, 3H), 4.58 (br s, 2H), 5.11 (br s, 1H), 8.27 (s, 1H); LC-MS: MH$^+$=172/174.

Preparation of
4-chloro-2-chloromethyl-3,5-dimethylpyridinium chloride

To a solution of 4-chloro-2-hydroxymethyl-3,5-dimethylpyridine (60.7 g, 354 mmol) and DMF (0.25 mL, 3.54 mmol) in toluene (200 mL) was added thionyl chloride (26.9 mL, 371 mmol) over 2 h at 15-30° C. After stirring for 2 more h at ambient temperature, ethanol (6 mL) was added to the thick slurry. The solids were filtered off at about 10° C., washed with toluene (80 mL) and dried at 40° C. in vacuo to give 4-chloro-2-chloromethyl-3,5-dimethylpyridinium chloride as an off-white solid (m. p. 195-196° C.); yield 66.5 g (84%).

$^1$H-NMR (200 MHz, DMSO-d6): δ=2.36 (s, 3H), 2.46 (s, 3H), 4.93 (s, 2H), 8.44 (s, 1H), 8.79 (br s, 1H); LC-MS: MH$^+$=190/192/194.

Example 41

5-Trideuteriomethoxy-2-[(4-chloro-3,5-dimethyl-2-pyridinyl)methylthio]-1H-benzimidazole At 55-65° C., a solution of 4-chloro-2-chloromethyl-3,5-dimethylpyridinium chloride (12.6 g, 55.6 mmol) in water (21 mL) was added over 2 h to a mixture of 5-trideuteriomethoxy-1H-benzimidazole-2-thiol (9.50 g, 51.8 mmol), toluene (47 mL), water (23 mL) and 40% aqueous NaOH (14 mL). Stirring at 60° C. was continued for 16 h before the reaction mixture was cooled to about 10° C. The precipitate was filtered off, washed with toluene (17 mL) and re-pulped in water (132 mL). Filtration followed by an aqueous rinse (70 mL) and drying at 35° C. in vacuo gave 5-trideuteriomethoxy-2-[(4-chloro-3,5-dimethyl-2-pyridinyl)methylthio]-1H-benzimidazole mono hydrate (KF=5.0%) as an off-white solid (m. p. 99-102° C.); yield 15.1 g (82%).

$^1$H-NMR (200 MHz, DMSO-d6): δ=2.30 (s, 3H), 2.43 (s, 3H), 4.72 (s, 2H), 6.76 (dd, 8.7 Hz, 2.5 Hz, 1H), 6.97 (br s, 1H), 7.35 (d, 8.7 Hz, 1H), 8.28 (s, 1H), 12.47 (br s, 1H); LC-MS: MH$^+$=337/339.

Example 42

5-Methoxy-2-[(4-chloro-3,5-dimethyl-2-pyridinyl)methylthio]-1H-benzimidazole

Starting from 5-methoxy-1H-benzimidazole-2-thiol (24.0 g, 111 mmol) and following the procedure described under Example 41, 5-methoxy-2-[(4-chloro-3,5-dimethyl-2-pyridinyl)methylthio]-1H-benzimidazole mono hydrate (KF=5.2%) was obtained as an off-white solid (m. p. 100-102° C.); yield 34.8 g (89%).

$^1$H-NMR (200 MHz, DMSO-d6): δ=2.30 (s, 3H), 2.43 (s, 3H), 4.72 (s, 2H), 6.76 (dd, 8.7 Hz, 2.5 Hz, 1H), 6.98 (br s, 1H), 7.35 (d, 8.7 Hz, 1H), 8.28 (s, 1H), 12.41 (br s, 1H); LC-MS: MH$^+$=334/336.

Example 43

5-Trideuteriomethoxy-2-[(4-methoxy-3,5-dimethyl-2-pyridinyl)methylthio]-1H-benzimidazole At 60-65° C., to a solution of 5-trideuteriomethoxy-2-[(4-chloro-3,5-dimethyl-2-pyridinyl)methylthio]-1H-benzimidazole mono hydrate (5.20 g, 14.7 mmol) in NMP (30 mL) was added over 1.5 h solid sodium methoxide (5.80 g, 104 mmol) in about 10 equal portions. Stirring at 60° C. was continued for 16 h, then the reaction mixture was heated at 70° C. for 24 h and, finally, at 80° C. for 4 h. After dilution with water (200 mL) and addition of 10% aqueous HCl (10 mL), the resulting dark brown solution was extracted twice with toluene (100+40 mL). The combined organic phase was washed successively with 5% aqueous NaOH (2×200 mL) and water (100 mL) before being evaporated to dryness. The residue was taken up in hot toluene (50 mL), subjected to a clear filtration and, again, evaporated to dryness. Finally, crystallization from TBME/toluene 10:1 (33 mL) yielded 5-trideuteriomethoxy-2-[(4-methoxy-3,5-dimethyl-2-pyridinyl)methylthio]-1H-benzimidazole as a white solid (m. p. 120-121° C.); yield 2.27 g (46%).

$^1$H-NMR (200 MHz, DMSO-d6): δ=2.20 (s, 3H), 2.27 (s, 3H), 3.73 (s, 3H), 4.65 (s, 2H), 6.75 (dd, 8.7 Hz, 2.5 Hz, 1H), 6.97 (br s, 1H), 7.35 (d, 8.7 Hz, 1H), 8.17 (s, 1H), 12.44 (br s, 1H); LC-MS: MH$^+$=333.

Example 44

5-Trideuteriomethoxy-2-[(3,5-dimethyl-4-trideuteriomethoxy-2-pyridinyl)methylthio]-1H-benzimidazole A solution of sodium trideuteriomethoxid was prepared by addition of methanol-d4 (1.70 mL, 41.5 mmol) at about 50° C. over 30 min to a suspension of sodium hydride (60% in mineral oil, 1.70 g, 41.5 mmol) in NMP (12 mL). After heating to 60° C., a solution of 5-trideuteriomethoxy-2-[(4-chloro-3,5-dimethyl-2-pyridinyl)methylthio]-1H-benzimidazole mono hydrate (2.10 g, 5.92 mmol) in NMP (4 mL) was added. Stirring was continued, first at 70° C. for 24 h, then at 85° C. for 5 h. Following the work-up procedure described under Example 41, 5-trideuteriomethoxy-2-[(3,5-dimethyl-4-trideuteriomethoxy-2-pyridinyl)methylthio]-1H-benzimidazole was obtained as a white solid (m. p. 120-121° C.); yield 0.55 g (28%).

$^1$H-NMR (200 MHz, DMSO-d6): δ=2.20 (s, 3H), 2.27 (s, 3H), 4.64 (s, 2H), 6.75 (dd, 8.7 Hz, 2.4 Hz, 1H), 6.89-7.38 (br m, 2H), 8.17 (s, 1H), 12.42 (br s, 1H); LC-MS: MH$^+$=336.

Example 45

5-Methoxy-2-[(3,5-dimethyl-4-trideuteriomethoxy-2-pyridinyl)methylthio]-1H-benzimidazole Starting from 5-methoxy-2-[(4-chloro-3,5-dimethyl-2-pyridinyl)methylthio]-1H-benzimidazole mono hydrate (24.0 g, 68.2 mmol) and following the procedure described under Example 44, 5-methoxy-2-[(3,5-dimethyl-4-trideuteriomethoxy-2-pyridinyl)methylthio]-1H-benzimidazole was obtained as a white solid (m. p. 119-121° C.); yield 8.72 g (38%).

$^1$H-NMR (200 MHz, DMSO-d6): δ=2.20 (s, 3H), 2.27 (s, 3H), 3.77 (s, 3H), 4.64 (s, 2H), 6.75 (dd, 8.7 Hz, 2.5 Hz, 1H), 6.98 (br s, 1H), 7.35 (br d, 8.6 Hz, 1H), 8.17 (s, 1H), 12.43 (br s, 1H); LC-MS: MH$^+$=333.

Example 46 rac-5-Trideuteriomethoxy-2-[(4-methoxy-3,5-dimethyl-2-pyridinyl)methylsulfinyl]-1H-benzimidazole 5-Trideuteriomethoxy-2-[(4-methoxy-3,5-dimethyl-2-pyridinyl)methylthio]-1H-benzimidazole (1.50 g, 4.51 mmol) was dissolved in CH$_2$Cl$_2$ (15 mL) and cooled to −55 to −40° C. At this temperature, a solution of 3-chloroperoxybenzoic acid (wet, 77% strength, 1.12 g, 5.00 mmol) in CH$_2$Cl$_2$ (8 mL) was slowly added over 1.5 h. After one more h at −55 to −40° C., triethylamine (0.87 mL, 6.28 mmol) and a 1:1 mixture of 6% aqueous Na$_2$CO$_3$ and 2% aqueous Na$_2$S$_2$O$_3$ (10 mL) were successively added while allowing the mixture to warm to about 0° C. Stirring was continued for 1 h at ambient temperature. The phases were separated, and the organic layer was washed twice with a 1:1 mixture of 6% aqueous Na$_2$CO$_3$ and 2% aqueous Na$_2$S$_2$O$_3$ and once with water (10 mL each) before being evaporated to dryness. The resulting residue was crystallized from ethyl acetate (6.0 mL) to give rac-5-trideuteriomethoxy-2-[(4-methoxy-3,5-dimethyl-2-pyridinyl)methylsulfinyl]-1H-benzimidazole as a white solid (m. p. 150-152° C., decomp.); yield 1.27 g (81%).

$^1$H-NMR (200 MHz, DMSO-d6): Y=2.17 (s, 3H), 2.20 (s, 3H), 3.69 (s, 3H), 4.67 (d, 13.6 Hz, 1H), 4.77 (d, 13.5 Hz, 1H), 6.92 (dd, 8.9 Hz, 2.4 Hz, 1H), 7.09 (br s, 1H), 7.54 (br d, 8.9 Hz, 1H), 8.18 (s, 1H), 13.39 (br s, 1H); LC-MS: MH$^+$=349.

Example 47 rac-5-Trideuteriomethoxy-2-[(3,5-dimethyl-4-trideuteriomethoxy-2-pyridinyl)methylsulfinyl]-1H-benzimidazole Starting from 5-trideuteriomethoxy-2-[(3,5-dimethyl-4-trideuteriomethoxy-2-pyridinyl)methylthio]-1H-benzimidazole (1.20 g, 3.57 mmol) and following the procedure described under Example 46, rac-5-trideuteriomethoxy-2-[(3,5-dimethyl-4-trideuteriomethoxy-2-pyridinyl)methylsulfinyl]-1H-benzimidazole was obtained as a white solid (m. p. 147-148° C., decomp.); yield 0.90 g (72%).

$^1$H-NMR (200 MHz, DMSO-d6): δ=2.16 (s, 3H), 2.20 (s, 3H), 4.67 (d, 13.5 Hz, 1H), 4.77 (d, 13.5 Hz, 1H), 6.90-7.55 (br m, 3H), 8.18 (s, 1H), 13.39 (br s, 1H); LC-MS: MH$^+$=352.

Example 48 rac-5-Methoxy-2-[(3,5-dimethyl-4-trideuteriomethoxy-2-pyridinyl)methylsulfinyl]-1H-benzimidazole Starting from 5-methoxy-2-[(3,5-dimethyl-4-trideuteriomethoxy-2-pyridinyl)methylthio]-1H-benzimidazole (1.00 g, 3.01 mmol) and following the procedure described under Example 46, rac-5-methoxy-2-[(3,5-dimethyl-4-trideuteriomethoxy-2-pyridinyl)methylsulfinyl]-1H-benzimidazole was obtained as a white solid (m. p. 143-144° C., decomp.); yield 0.86 g (82%).

$^1$H-NMR (200 MHz, DMSO-d6): δ=2.17 (s, 3H), 2.20 (s, 3H), 3.81 (s, 3H), 4.67 (d, 13.6 Hz, 1H), 4.77 (d, 13.5 Hz, 1H), 6.90-7.55 (br m, 3H), 8.18 (s, 1H), 13.40 (br s, 1H); LC-MS: MH$^+$=349.

Example 49

(S)-5-Trideuteriomethoxy-2-[(3,5-dimethyl-4-trideuteriomethoxy-2-pyridinyl)methylsulfinyl]-1H-benzimidazole sodium salt At room temperature, 5-trideuteriomethoxy-2-[(3,5-dimethyl-4-trideuteriomethoxy-2-pyridinyl)methylthio]-1H-benzimidazole (3.02 g, 9.00 mmol) and (+)-L-tartaric acid bis-(N-pyrrolidinamide) (0.92 g, 3.60 mmol) were suspended in 35 mL of methyl isobutyl ketone. The mixture was heated to 40° C. and about 8 mL of solvent were evaporated under vacuum to remove water. Then, zirconium (IV) n-propoxide (0.40 mL, 70% in n-propanol, 0.90 mmol) was added and stirring at 40° C. was continued for one more hour. After cooling to 30° C., N-ethyldiisopropylamine (0.11 mL, 0.63 mmol) and cumene hydroperoxide (1.52 mL, ~80% strength, 8.55 mmol) were added. After stirring for about 20 h at 30° C., the clear reaction mixture was diluted with methyl isobutyl ketone (8.5 mL) and quenched with sodium thiosulphate (0.11 g) in saturated sodium bicarbonate solution (15 mL).

After phase separation, the organic layer was washed twice with saturated sodium bicarbonate solution (7.5 mL each). To the organic phase, water was added (25 mL), and the pH was adjusted to pH=12.5-13 using 40% aqueous NaOH (0.71 mL). The organic layer was extracted twice more with water (7.5 mL) at pH 12.5-13 (through addition of prerequisite amount of 40% aqueous NaOH). The combined organic phase was washed with dichloromethane (15 mL). Then, the pH was adjusted to about 10 with potassium dihydrogen phosphate and the aqueous solution was extracted with dichloromethane (once 40 mL and twice 10 mL). Evaporation of the organic phase to dryness gave (S)-5-trideuteriomethoxy-2-[(3,5-dimethyl-4-trideuteriomethoxy-2-pyridinyl)methylsulfinyl]-1H-benzimidazole as a brownish oil, which was further purified by formation of the corresponding sodium salt. To this end, the crude product was taken up in methyl isobutyl ketone (15 mL) and isopropanol (1.5 mL). Then, 40% aqueous NaOH (0.63 mL) was added and the resulting suspension was cooled to 0° C. The solids were filtered off, washed with methyl isobutyl ketone (twice 2.0 mL) and dried at 45° C. in vacuo to give (S)-5-trideuteriomethoxy-2-[(3,5-dimethyl-4-trideuteriomethoxy-2-pyridinyl)methylsulfinyl]-1H-benzimidazole sodium salt as an off-white solid (m. p. 224-225° C. (decomp.), KF=1.5%); yield 2.05 g (61%).

Chiral HPLC: >97.0% ee; optical rotation: $[\alpha]_D=-440$ (MeOH, c=0.53), $[\alpha]_D=+39°$ (H$_2$O, c=0.39).

$^1$H-NMR (200 MHz, DMSO-d6): δ=2.18 (s, 3H), 2.21 (s, 3H), 4.39 (d, 12.9 Hz, 1H), 4.63 (d, 12.9 Hz, 1H), 6.54 (dd, 8.7 Hz, 2.5 Hz, 1H), 6.98 (d, 2.5 Hz, 1H), 7.32 (br d, 8.6 Hz, 1H), 8.23 (s, 1H).

Example 50

Bis-[(S)-5-trideuteriomethoxy-2-[(3,5-dimethyl-4-trideuteriomethoxy-2-pyridinyl)methylsulfinyl]-1H-benzimidazole] magnesium salt Starting from (S)-5-trideuteriomethoxy-2-[(3,5-dimethyl-4-trideuteriomethoxy-2-pyridinyl)methylsulfinyl]-1H-benzimidazole sodium salt (200 mg, KF=1.5%, 0.528 mmol) and following the procedure described under Example 35, bis-[(S)-5-trideuteriomethoxy-2-[(3,5-dimethyl-4-trideuteriomethoxy-2-pyridinyl)methylsulfinyl]-1H-benzimidazole] magnesium salt was obtained as a white solid (m. p. 161-162° C. (decomp.); KF=1.5%); yield 132 mg (68%).

Chiral HPLC: >97.0% ee; optical rotation: $[\alpha]_D=-120°$ (MeOH, c=0.50).

By proper combination of the procedures described above, further compounds of the present invention are also accessible:

For example, 4-chloro-2-chloromethyl-3-methylpyridinium chloride could be reacted with 1H-benzimidazole-2-thiol according to the procedure described under Example 12 to give 2-[(4-chloro-3-methyl-2-pyridinyl)methylthio]-1H-benzimidazole. Conversion of this product with, for instance, 1,1-dideuterio-3-methoxy-1-propanol or 1,1-dideuterio-2,2,2-trifluoroethanol following the protocol described under Example 14 would then give rise to formation of 2-[(4-(1,1-dideuterio-3-methoxyprop-1-oxy)-3-methyl-2-pyridinyl)methylthio]-1H-benzimidazole and 2-[(4-(1,1-dideuterio-2,2,2-trifluoroethoxy)-3-methyl-2-pyridinyl)methylthio]-1H-benzimidazole, respectively. Finally, oxidation of these compounds according to the procedure used in Example 46 would provide rac-2-[(4-(1,1-dideuterio-3-methoxypropan-1-oxy)-3-methyl-2-pyridinyl)methylsulfinyl]-1H-benzimidazole and rac-2-[(4-(1,1-dideuterio-2,2,2-trifluoroethoxy)-3-methyl-2-pyridinyl)methylsulfinyl]-1H-benzimidazole, respectively.

As a further example, 4-chloro-2-chloromethyl-3,5-dimethylpyridinium chloride could be reacted with 5-methoxy-1H-imidazo[4,5-b]pyridine-2-thiol according to the procedure described under Example 39 to give 5-methoxy-2-[(4-chloro-3,5-dimethyl-2-pyridinyl)methylthio]-1H-imidazo[4,5-b]pyridine. Conversion of this product with methanol-d4 following the protocol described under Example 44 would then give rise to formation of 5-methoxy-2-[(3,5-dimethyl-4-trideuteriomethoxy-2-pyridinyl)methylthio]-1H-imidazo[4,5-b]pyridine, which, in turn, could be oxidized according to the procedure used in Example 46 to rac-5-methoxy-2-[(3,5-dimethyl-4-trideuteriomethoxy-2-pyridinyl)methylsulfinyl]-1H-imidazo[4,5-b]pyridine.

Commercial Utility

The compounds of the general formulae 1 and 10 and their salts and solvates, preferably hydrates, and the solvates, preferably hydrates of the salts (hereinafter "compounds of the invention") have useful pharmacological properties, rendering them commercially utilizable. In particular, they have a pronounced inhibitory effect on the secretion of gastric acid and excellent gastrointestinal protective action in warm-blooded animals, in particular man. Here, the compounds according to the invention are distinguished by a highly selective action, an advantageous duration of action, a particularly high bioavailability, a metabolisation profile that is uniform among different individuals, the lack of significant side-effects and a wide therapeutic spectrum.

In this context, "gastrointestinal protection" is to be understood as the prevention and treatment of gastrointestinal disorders, in particular gastrointestinal inflammatory disorders and lesions (such as, for example, Ulcus ventriculi, Ulcus duodeni, gastritis, irritable bowel owing to an increased production of acid or as a result of pharmaceutical compositions, GERD, Crohn's disease, IBD) which may be caused, for example, by microorganisms (for example *Helicobacter pylori*), bacterial toxins, pharmaceutical compositions (for example certain antiphlogistics and antirheumatic drugs), chemicals (for example ethanol), gastric acid or stress.

With their excellent properties, the compounds according to the invention, in various models for the determination of antiulcerogenic and antisecretory properties, surprisingly prove to be clearly superior to the prior art compounds, in particular with respect to their pharmacokinetic properties. These improved pharmacokinetic properties allow for example a reduction of the amount of a compound according to the invention, which is needed for treatment or prophylaxis. Or by using the same amount of the compound according to the invention as done for the prior art compounds a longer duration of action may be achieved. Related with these properties are advantages concerning patient safety or economical aspects, e.g. like drug costs etc. Owing to these properties, the compounds according to the invention are highly suitable for use in human and veterinary medicine, where they are used, in particular, for the treatment and/or prophylaxis of gastrointestinal disorders.

Accordingly, the invention furthermore provides the use of the compounds according to the invention for the treatment and/or prophylaxis of the abovementioned diseases.

The invention also embraces the use of the compounds according to the invention for preparing pharmaceutical compositions used for the treatment and/or prophylaxis of the abovementioned diseases.

The invention also provides pharmaceutical compositions comprising the compounds according to the invention. In particular, the invention provides pharmaceutical compositions for oral use in solid form, containing the compounds of formulae 1, 1a, 1b, 10, 10a or 10b in the form of their salts, in particular in the form of a sodium or magnesium salt, and/or in the form of a hydrate of such salt.

The pharmaceutical compositions are prepared by processes known per se which are familiar to the person skilled in the art. As pharmaceutical compositions, the compounds according to the invention are employed either as such or, preferably, in combination with suitable pharmaceutical auxiliaries or carriers in the form of tablets, coated tablets, capsules, suppositories, plasters (for example as TTS), emulsions, suspensions or solutions, where the content of active compound is advantageously from about 0.1 to about 95% and where it is possible to produce pharmaceutical dosage forms (for example flow-release forms or enteric forms) which, by the appropriate choice of auxiliaries and carriers, are tailored for the active compound and/or the desired onset of action and/or the duration of action.

The auxiliaries or carriers suitable for the desired pharmaceutical formulations are known to the person skilled in the art. In addition to solvents, gel formers, suppository bases, tabletting auxiliaries and other carriers for active compounds, it is possible to use, for example, antioxidants, dispersants, emulsifiers, antifoams, flavour-masking agents, preservatives, solubilizers, colorants or, in particular, permeation promoters and complex formers (for example cyclodextrins).

The compounds according to the invention can be administered orally, parenterally or percutaneously.

In human medicine, it has generally been found to be advantageous to administer the compounds according to the invention, when given orally, in a daily dose of from about 0.01 to about 1, preferably about 0.02 to about 0.5 and in particular about 0.04 to about 0.3, mg/kg of body weight [calculated on the basis of the compounds according to the invention in free form, i.e. not in salt form (="free compound"], if appropriate in the form of a plurality of, preferably 1 to 4, individual doses, to obtain the desired result. For parenteral treatment, it is possible to use similar or (in particular when the active compounds are administered intravenously) generally lower dosages. The optimum dosage and the type of administration of the active compounds required in each case can easily be determined by the person skilled in the art.

A further aspect of the invention is thus a pharmaceutical composition, comprising one or more compound according to the invention together with one or more customary auxiliaries, where the single dose comprises from about 2 to about 60 mg of the free compound.

A further aspect of the invention is a pharmaceutical composition, comprising one or more compound according to the invention together with one or more customary auxiliaries, where the single dose comprises from about 4 to about 40 mg of the free compound.

A further aspect of the invention is the use of the compounds according to the invention for treating gastrointestinal disorders.

A further aspect of the invention is the use of the compounds according to the invention for the manufacture of pharmaceutical composition for the treatment or prophylaxis of gastrointestinal disorders.

A further aspect of the invention is a method of treating gastrointestinal disorders by administering a pharmaceutical composition comprising one or more compounds according to the invention.

Has only a base in 1416 specification!!!??

A further aspect of the invention is the use of the compounds according to the invention for treating gastrointestinal disorders in patients who are slow metabolizers.

A further aspect of the invention is the use of the compounds according to the invention hereof for treating gastrointestinal disorders in patients who have a risk of drug interactions.

A further aspect of the invention is the use of the compounds according to the invention for treating gastrointestinal disorders in patients who need an inhibition of acid secretion for an extended period of time.

A further aspect of the invention is a pharmaceutical composition for treating gastrointestinal disorders for use in patients who are slow metabolizers, comprising one or more compound according to the invention together with one or more customary auxiliaries, where the single dose comprises from about 2 to about 60 mg of free compound.

A further aspect of the invention is a pharmaceutical composition for treating gastrointestinal disorders for use in patients who are slow metabolizers, comprising one or more compound according to the invention together with one or more customary auxiliaries, where the single dose comprises from about 4 to about 40 mg of free compound.

A further aspect of the invention is a pharmaceutical composition for treating gastrointestinal disorders for use in patients who have a risk of drug interactions, comprising one or more compound according to the invention together with one or more customary auxiliaries, where the single dose comprises from about 2 to about 60 mg of free compound.

A further aspect of the invention is a pharmaceutical composition for treating gastrointestinal disorders for use in patients who have a risk of drug interactions, comprising one or more compound according to the invention together with one or more customary auxiliaries, where the single dose comprises from about 4 to about 40 mg of free compound.

A further aspect of the invention is a pharmaceutical composition for treating gastrointestinal disorders for use in patients who need an inhibition of acid secretion for an extended period of time, comprising one or more compound according to the invention together with one or more customary auxiliaries, where the single dose comprises from about 2 to about 60 mg of free compound.

A further aspect of the invention is a pharmaceutical composition for treating gastrointestinal disorders for use in patients who need an inhibition of acid secretion for an extended period of time, comprising one or more compound according to the invention together with one or more customary auxiliaries, where the single dose comprises from about 4 to about 40 mg of free compound.

A further aspect of the invention is a pharmaceutical composition for treating gastrointestinal disorders for use in patients who are slow metabolizers, comprising in an oral solid application form one or more salt according to the invention or a hydrate thereof together with one or more customary auxiliaries, where the single dose comprises from about 2 to about 60 mg of free compound.

A further aspect of the invention is a pharmaceutical composition for treating gastrointestinal disorders for use in patients who are slow metabolizers, comprising in an oral solid application form one or more salt according to the invention or a hydrate thereof together with one or more customary auxiliaries, where the single dose comprises from about 4 to about 40 mg of free compound.

A further aspect of the invention is a pharmaceutical composition for treating gastrointestinal disorders for use in patients who have a risk for drug interactions, comprising in an oral solid application form one or more salt according to the invention or a hydrate thereof together with one or more customary auxiliaries, where the single dose comprises from about 2 to about 60 mg of free compound.

A further aspect of the invention is a pharmaceutical composition for treating gastrointestinal disorders for use in patients who have a risk for drug interactions, comprising in an oral solid application form one or more salt according to the invention or a hydrate thereof together with one or more customary auxiliaries, where the single dose comprises from about 4 to about 40 mg of free compound.

A further aspect of the invention is a pharmaceutical composition for treating gastrointestinal disorders for use in patients who need an inhibition of acid secretion for an extended period of time, comprising in an oral solid application form one or more salt according to the invention or a hydrate thereof together with one or more customary auxiliaries, where the single dose comprises from about 2 to about 60 mg of free compound.

A further aspect of the invention is a pharmaceutical composition for treating gastrointestinal disorders for use in patients who need an inhibition of acid secretion for an extended period of time, comprising in an oral solid application form one or more salt according to the invention or a hydrate thereof together with one or more customary auxiliaries, where the single dose comprises from about 4 to about 40 mg of free compound.

If the compounds according to the invention are to be used for treating the abovementioned diseases, the pharmaceutical preparations may also comprise one or more pharmacologically active ingredients from other groups of pharmaceutical compositions. Examples that may be mentioned include tranquilizers (for example from the group of the benzodiazepines, e.g., diazepam), spasmolytic drugs (e.g., bietamiverine or camylofine), anticholinergic drugs (e.g., oxyphencyclimine or phencarbamide), local anesthetics (e.g., tetracaine or procaine), and optionally also enzymes, vitamins or amino acids.

In this context, particular emphasis is given to the combination of the compounds according to the invention with other pharmaceuticals which buffer or neutralize gastric acid or which inhibit the secretion of acid, such as, for example, antacids (such as, for example, magaldrate) or $H_2$ blockers (e.g., cimetidine, ranitidine), and with gastrin antagonists with the aim to enhance the main action in an additive or superadditive sense and/or to eliminate or reduce side-effects or to obtain a more rapid onset of action. Mention may also be made of the fixed or free combination with NSAIDs (such as, for example, etofenamate, diclofenac, indometacin, ibuprofen or piroxicam) for preventing the gastrointestinal damage caused by the NSAIDs, or with compounds, which modify gastrointestinal motility, or with compounds, which reduce the incidence of transient lower esophageal sphincter relaxation (TLOSR), or with antibacterial substances (such as, for example, cephalosporins, tetracyclins, penicillins, macrolides, nitroimidazoles or else bismuth salt) for controlling *Helicobacter pylori*. Antibacterial combination partners that may be mentioned include, for example, mezlocillin, ampicillin, amoxicillin, cefalothin, cefoxitin, cefotaxim, imipenem, gentamycin, amicacin, erythromycin, ciprofloxacin, metronidazole, clarithromycin, azithromycin and combinations thereof (e.g., clarithromycin+metronidazole or amoxicillin+clarithromycin).

In practicing the present invention, the compounds according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics as those mentioned above.

The term "combination" according to this invention may be present as a fixed combination, a non-fixed combination or a kit-of-parts.

A "fixed combination" is defined as a combination wherein a first active ingredient and a second active ingredient are present together in one unit dosage or in a single entity. One example of a "fixed combination" is a pharmaceutical composition wherein the said first active ingredient and the said second active ingredient are present in admixture of simultaneous administration, such as in a formulation. Another example of a "fixed combination" is a pharmaceutical composition wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination the said first active ingredient and the said second active ingredient are present separately. The components of the kit-of-parts may be administered separately, sequentially, simultaneously or chronologically staggered.

Pharmacology

Metabolisation in Liver Microsomes

Materials and Methods

Pantoprazole or examples 1 or 2 (10 μM each) were incubated with liver microsomes (source: all from GenTest except Mini Pig from TEBU),incubation in 1 mg/ml protein, 100 mM Tris-HCl, pH 7.4, 1 mM $NADPH_2$). Reaction was terminated after 90 minutes by liquid nitrogen, the parent compound was detected by HPLC (10 mM $KH_2PO_4$, pH 7.4, acetonitril gradient 20-44%).

TABLE 1

Metabolism of H-pantoprazole versus deutero-compounds (example 1, 2) with microsomes after 90 minutes incubation time (species dependent).

| | Percent of compound metabolized | | | | |
|---|---|---|---|---|---|
| Species | H-Pantoprazole | Example 1 | Example 2 | Example 1/ Pantoprazole | Example 2/ Pantoprazole |
| Rat | 61 | 35 | 17 | 0.57 | 0.28 |
| Dog | 20 | 12 | 10 | 0.60 | 0.50 |
| Human | 28 | 14 | 15 | 0.50 | 0.54 |
| Mouse | 62 | 36 | 17 | 0.58 | 0.27 |
| Guinee pig | 78 | 59 | 54 | 0.75 | 0.69 |
| Monkey | 73 | 47 | 35 | 0.64 | 0.48 |
| Mini Pig | 26 | 19 | 19 | 0.73 | 0.73 |

Metabolic Clearance

In order to evaluate the properties of the compounds according to the invention the compounds' intrinsic clearances in recombinant human cytochrome P450 (CYP) isoenzymes CYP1A2, CYP2C8, CYP2C19, CYP2D6, CYP3A4, and CYP3A5 were determined.

Materials and Methods

Compounds as described in examples 5, 6, 22, 24, 25, 30, 32, 34, 35, 44, 45, 46 and 47, the non-deuterated racemic omeprazole, its (S)-enantiomer and non-deuterated pantoprazole and its enantiomers were incubated in a buffer containing 1 nmol/mL recombinant P450 (Cypex, Dundee, UK), 4 mg/mL microsomal protein, 100 mMol/L Tris-HCl (pH 7.4) and 1 mMol/L NADPH for 0, 3, 6, 12, and 15 or 30 minutes at 37° C. Incubations were carried out in triplicate. For incubations with CYP2C19 the P450 concentration was lowered to 0.5 nmol/mL and the incubation interval changed to 0, 1, 2, 3, 4, and 5 min. The intrinsic clearance was determined based on the rate of disappearance of parent compound. Pantoprazole, omeprazole and the deuterated analogues were determined by HPLC-UV. The lower limit of assay resolution based on experimental variability was 17.6 µl/min/nmol P450.

Results

CYP2C19 and CYP3A4 were found to contribute to the oxidative metabolism of omeprazole, pantoprazole and their deuterated analogues. All other cytochrome P450 isoenzymes (CYP1A2, CYP2C8, CYP2C9, CYP2D6, CYP3A5) did not contribute to the metabolism of any of the compounds investigated above the lower limit of assay resolution.

Formation Kinetics of pantoprazole M2 (5-(difluoromethoxy)-2-[[(3-methoxy-4-sulfate-2-pyridyl)-methyl]sulfinyl]-1H-benzimidazole)

Following the evaluation of the metabolic clearance of the compounds according to the invention via P450 enzymes, the formation kinetics of the main metabolite identified in humans, i.e. M2 (5-(difluoromethoxy)-2-[[(3-methoxy-4-sulfate-2-pyridyl)-methyl]sulfinyl]-1H-benzimidazole) was determined. Because the generation of M2 involves the oxidation of the 4-methoxy-pyridyl group by CYP2C19 and subsequent conjugation with 3'-phosphoadenosine-5'-phosphosulfate (PAPS) by an unidentified sulphotransferase, human cryopreserved hepatocytes were used since both phase I and phase II enzymes are functional in this in vitro system.

Materials and Method

Compounds as described in examples 5, 6, 22, 24, 25 and 30 and further racemic [$^1$H]pantoprazole sodium sesquihydrate and the corresponding S- and R-enantiomers were incubated in Krebs Henseleit Puffer (KHB), containing 84 µg/mL amikacin, 1 mMol/L calcium chloride, 20 mMol/L Hepes, 4.2 µMol/L hepatonic acid, 28.5 mMol/L sodium bicarbonate, and human cryopreserved hepatocytes (10 donor pool, InVitro Technologies, Baltimore, Md. USA) at a concentration of $10^6$ cells/mL. M2 formation rate under these conditions was linear up to 60 min. The M2 formation rate was determined at nine different compound concentrations (0, 0.5, 1.0, 2.5, 5.0, 10.0, 25.0, 50.0 and 100 µMol/L) incubated in duplicate for 60 min at 37° C. M2 was quantified using LC-MS/MS. M2 isolated from human urine was used as an external standard. The concentration to reach the half-maximal formation rate ($K_M$-value) and the maximal formation rate ($V_{max}$) were obtained by non-linear regression analysis using the Michaelis-Menten equation. The intrinsic clearance ($Cl_{int}$) was obtained dividing $V_{max}$ over $K_M$.

Results

The formation of M2 from pantoprazole, its enantiomers and from compounds as described in examples 5, 6, 22, 24, 25 and 30 appeared to be inhibited by substrate concentrations above 100 µM. Therefore, the data for incubations with 100 and 250 µM substrate concentrations were excluded from the calculation of $K_m$ and $V_{max}$. The formation of M2 from racemic [$^1$H]pantoprazole and enantiomers exhibited stereospecific differences (FIG. 1A). Racemic, (R), and (S)-analogues (examples 6, 30 and 5) deuterated in the 4-methoxy-pyridyl position exhibited formation rates that were at least 2.5-fold reduced compared to their non-deuterated counterparts (FIG. 1B). The intrinsic clearances of racemic, (R), and (S)-analogues deuterated in the 4-methoxy-pyridyl position (examples 6, 30 and 5) were at least 4.7-fold reduced compared to their non-deuterated counterparts (Table 2). The stereospecific differences in M2 formation rates observed for the [$^1$H] pantoprazole analogues were less pronounced for analogues deuterated in the 4-methoxy-pyridyl position (FIG. 1B). Surprisingly, the reduction in M2 formation rate as compared to the non-deuterated compounds seems to dependent on the position of the trideuteriomethoxy-group in the pyridyl moiety of the molecule (FIG. 2). Increasing the number of [$^1$H] atoms substituted by [$^2$H] atoms in the 4-methoxy-pyridyl position of the molecule ([$^1$H], [$^2$H$_1$] example 25, [$^2$H$_2$] example 24, and [$^2$H$_3$] example 6) decreased M2 formation rates (FIG. 3).

TABLE 2

Intrinsic clearance ($Cl_{int}$) in pooled human hepatocytes obtained upon incubation with pantoprazole and compounds according to the invention.

| Compound | $Cl_{int}$ [µl/min/10$^6$ cells] | |
|---|---|---|
| | | % Σ $C_{lint}$ rac. pantoprazole |
| rac. pantoprazole Na 1.5 H$_2$O | 27.9 | 100 |
| Example 6 | 5.1 | 20 |
| Example 22 | 22.0 | 79 |
| Example 24 | 13.5 | 48 |
| Example 25 | 17.7 | 63 |
| | | % Σ $C_{lint}$ (R)-pantoprazole |
| (R)-pantoprazole Na 1.5 H$_2$O | 25.7 | 100 |
| Example 30 | 5.5 | 21 |
| | | % Σ $C_{lint}$ (S)-pantoprazole |
| (S)-pantoprazole Na 1.5 H$_2$O | 16.1 | 100 |
| Example 5 | 3.4 | 21 |

Formation Kinetics of omeprazole 5-hydroxy-omeprazole and 5-(difluoromethoxy)-2-[[(3-methoxy-4-sulfate-2-pyridyl)-methyl]sulfinyl]-1H-benzimidazole Following the evaluation of the metabolic clearance of the compounds according to the invention via P450 enzymes, the formation kinetics of the main metabolite identified in humans, i.e. 5-hydroxy-omeprazole (5-methoxy-2-[[(4-methoxy-3-methyl-5-hydroxymethyl-2-pyridinyl)-methyl]sulfinyl]-1H-benzimidazole) for omeprazole and 5-(difluoromethoxy)-2-[[(3-methoxy-4-sulfate-2-pyridyl)-methyl]sulfinyl]-1H-benzimidazole for pantoprazole was determined. The generation of 5-hydroxy-omeprazole and 5-(difluoromethoxy)-2-[[(3-methoxy-4-sulfate-2-pyridyl)-methyl]sulfinyl]-1H-benzimidazole is predominantly carried out by CYP2C19. We chose pooled human cryopreserved hepatocytes as the more advanced in vitro system compared to human liver microsomes, because all major drug metabolizing enzymes (phase I, phase II, hydrolases) are functional in this in vitro system.

Materials and Methods

Compounds as described in examples 22, 32, 24, 25, 36, 37, 46, 47, 48 and 49 and the non-deuterated racemic omeprazole, its (S)-enantiomer and non-deuterated pantoprazole and its enantiomers were incubated in Krebs Henseleit Puffer (KHB), containing 84 µg/mL amikacin, 1 mMol/L calcium chloride, 20 mMol/L Hepes, 4.2 µMol/L hepatonic acid, 28.5 mMol/L sodium bicarbonate, and human cryopreserved hepatocytes (10 donor pool, InVitro Technologies, Baltimore, Md. USA) at a concentration of $10^6$ cells/mL. 5-hydroxy-omeprazole and 5-(difluoromethoxy)-2-[[(3-methoxy-4-sulfate-2-pyridyl)-methyl]sulfinyl]-1H-benzimidazole (M2) formation rates under these conditions were linear up to 60 min. The 5-hydroxy-omeprazole formation rate was determined at ten different compound concentrations (0, 1.0, 2.5, 5.0, 10.0, 25.0, 50.0, 100, 200 and 2500 µMol/L) incubated in duplicate for 60 min at 37° C. The 5-(difluoromethoxy)-2-[[(3-methoxy-4-sulfate-2-pyridyl)-methyl]sulfinyl]-1H-benzimidazole (M2) formation rate was determined at nine different compound concentrations (0, 0.5, 1.0, 2.5, 5.0, 10.0, 25.0, 50.0 and 100 µMol/L) incubated in duplicate for 60 min at 37° C. 5-hydroxy-omeprazole was quantified using LC-MS/MS. 5-hydroxy-omeprazole obtained from Ramidius A B, Lund, Sweden and 5-(difluoromethoxy)-2-[[(3-methoxy-4-sulfate-2-pyridyl)-methyl]sulfinyl]-1H-benzimidazole (M2) isolated from human urine were used as an external standard. The concentration to reach the half-maximal formation rate ($K_M$-value) and the maximal formation rate ($V_{max}$) were obtained by non-linear regression analysis using the Michaelis-Menten equation. The intrinsic clearance ($Cl_{int}$) was obtained dividing $V_{max}$ over $K_M$.

Results

Examples 47 and 48, both deuterated in the 4-methoxy-pyridinyl position exhibited formation rates that were about 1.5-fold reduced compared to non-deuterated omeprazole. There was no difference between the $K_M$-values of racemic [$^1$H], [$^2$H$_3$], and [$^2$H$_6$] omeprazole analogues that exceeded experimental variability (FIG. 4). Reduction in the 5-hydroxy-omeprazole formation rate was observed for example 48, but was surprisingly not found for example 46 (FIG. 4). Moreover, there was no difference in the formation rate between [$^2$H$_3$]omeprazole deuterated in the 4-methoxy-pyridinyl position (example 48) and [$^2$H$_6$]omeprazole additionally deuterated in the 5-methoxy-benzimidazole position (example 49, FIG. 6).The formation of 5-hydroxy-omeprazole from rac. [$^1$H]omeprazole and its (S)-enantiomer exhibited stereospecific differences, since the difference between the $K_M$ and $V_{max}$ values of racemic and (S)-omeprazole exceeded experimental variability. The substitution of six [$^1$H] atoms by [$^2$H] atoms in the 4-methoxy-pyridinyl and 5-methoxy-benzimidazole position of (S)-omeprazole (example 49), did not alter the intrinsic clearance ($Cl_{int}$) of 5-hydroxy-omeprazole (FIG. 6).

The formation of 5-(difluoromethoxy)-2-[[(3-methoxy-4-sulfate-2-pyridyl)-methyl]sulfinyl]-1H-benzimidazole (M2) from pantoprazole, its enantiomers and from compounds as described in examples 22, 32, 24, 25, 36 and 37 appeared to be inhibited by substrate concentrations above 100 µM. Therefore, the data for incubations with 100 and 250 µM substrate concentrations were excluded from the calculation of $K_m$ and $V_{max}$. The formation of M2 from racemic [1H]pantoprazole and enantiomers exhibited stereospecific differences (FIG. 5A). Racemic, (R), and (S)-analogues (examples 32, 36 and 37 deuterated in the 4-methoxy-pyridyl position exhibited formation rates that were at least 2.5-fold reduced compared to their non-deuterated counterparts (FIG. 5B). The intrinsic clearances of racemic, (R), and (S)-analogues deuterated in the 4-methoxy-pyridyl position (examples 32, 36 and 37) were at least 4.7-fold reduced compared to their non-deuterated counterparts (Table 3). The stereospecific differences in M2 formation rates observed for the [$^1$H] pantoprazole analogues were less pronounced for analogues deuterated in the 4-methoxy-pyridyl position (FIG. 5B). Surprisingly, the reduction in M2 formation rate as compared to the non-deuterated compounds seems to dependent on the position of the trideuteriomethoxy-group in the pyridyl moiety of the molecule (FIG. 7). Increasing the number of [$^1$H] atoms substituted by [$^2$H] atoms in the 4-methoxy-pyridyl position of the molecule ([$^1$H], [$^2$H$_1$] example 25, [$^2$H$_2$] example 24, and [$^2$H$_3$] example 32) decreased M2 formation rates.

TABLE 3

Intrinsic clearance ($Cl_{int}$)) in pooled human hepatocytes obtained upon incubation with pantoprazole and compounds according to the invention.

| Compound | $Cl_{int}$ [µl/min/$10^6$ cells] | |
|---|---|---|
| | | % Σ $C_{lint}$ rac. Omeprazole |
| rac. Omeprazole | 2.0 | 100 |
| Example 48 | 1.4 | 69 |
| Example 46 | 2.1 | 107 |
| Example 47 | 1.4 | 69 |
| (S)-omeprazole sodium | 0.7 | 37 |
| Example 49 | 0.8 | 40 |
| | | % Σ $C_{lint}$ rac. Pantoprazole |
| rac. pantoprazole Na 1.5 H$_2$O | 27.9 | 100 |
| Example 32 | 5.1 | 18 |
| Example 22 | 22.0 | 79 |
| Example 24 | 13.5 | 48 |
| Example 25 | 17.7 | 63 |
| | | % Σ $C_{lint}$ (R)-pantoprazole |
| (R)-pantoprazole Na 1.5 H$_2$O | 25.7 | 100 |
| Example 37 | 5.5 | 21 |
| | | % Σ $C_{lint}$ (S)-pantoprazole |
| (S)-pantoprazole Na 1.5 H$_2$O | 16.1 | 100 |
| Example 36 | 3.4 | 21 |

We claim:
1. A compound of formula 10

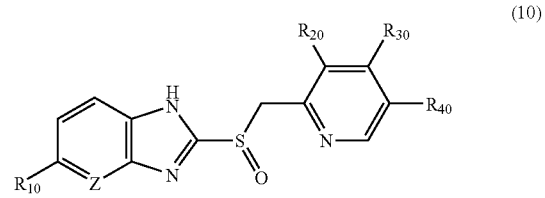

(10)

in which
R10 is hydrogen, difluoromethoxy or 1-4C-alkoxy,
R20 is 1-4C-alkyl or 1-4C-alkoxy,
R30 is 1-4C-alkyl, 1-4C-alkoxy, 2,2,2-trifluoroethoxy or 2-8C-alkoxyalkoxy,
R40 is hydrogen or 1-4C-alkyl,
Z is N,
or a salt or enantiomer thereof, wherein at least one hydrogen atom of R10, R20, R30, R40 or any combination of R10, R20, R30 and R40 is replaced by a deuterium atom.

2. A compound of formula 10 according to claim 1, wherein at least one of the hydrogen atoms of R30 is replaced by a deuterium atom and R30 is a 1-2C alkoxy group or a 2-5C-alkoxyalkoxy group.

3. A compound of formula 10 according to claim 1, wherein R20 is a 1-4C alkyl group and R30 is a 2-8C-alkoxyalkoxy group, and wherein at least one of the hydrogen atoms of R20, R30 or R20 and R30 is replaced by a deuterium atom.

4. A compound of formula 10 according to claim 1, wherein R10 is a 1-4C alkoxy group, R20 and R40 are a 1-4C alkyl group and R30 is a 1-4C-alkoxy group, and wherein at least one of the hydrogen atoms of R10, R30, R40 or any combination of R10, R30 and R40 is replaced by a deuterium atom.

5. A compound of formula 10 according to claim 1, wherein R10 is hydrogen, methoxy or difluoromethoxy, R20 is methyl or methoxy, R30 is methoxy, 2,2,2-trifluoroethoxy or methoxypropoxy, R40 is hydrogen or methyl and wherein at least one of the hydrogen atoms of R30 is replaced by a deuterium atom.

6. A compound of formula 10 according to claim 1, wherein R10 is methoxy, R20 and R40 are methyl and R30 is methoxy, wherein at least one of the hydrogen atoms of R10, R30, R40 or any combination of R10, R30 and R40 is replaced by a deuterium atom.

7. A compound of formula 10 according to claim 1, wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein at least one of the hydrogen atoms of R30 is replaced by a deuterium atom.

8. A compound of formula 10 according to claim 1, wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein at least two of the hydrogen atoms of R30 are replaced by a deuterium atom.

9. A compound of formula 10 according to claim 1, wherein R20 is a 1-4C alkyl group and R30 is a 2-8C-alkoxyalkoxy group, wherein all hydrogen atoms of R20, R30 or R20 and R30 are replaced by deuterium atoms.

10. A compound of formula 10 according to claim 1, wherein R10 is a 1-4C alkoxy group, R20 and R40 are a 1-4C alkyl group and R30 is a 1-4C-alkoxy group, wherein all hydrogen atoms of R10, R30, R40 or any combination of R10, R30 and R40 are replaced by deuterium atoms.

11. A compound of formula 10 according to claim 1, wherein all hydrogen atoms of R30 are replaced by deuterium atoms and wherein R30 is methoxy, 2,2,2-trifluoroethoxy or methoxypropoxy.

12. A compound of formula 10 according to claim 1, wherein R10 is methoxy, R20 and R40 are methyl and R30 is methoxy, wherein all hydrogen atoms of R10, R30, R40 or any combination of R10, R30 and R40 are replaced by deuterium atoms.

13. A compound of formula 10 according to claim 1, wherein R10 is hydrogen, methoxy or difluoromethoxy, R20 is methyl or methoxy, R30 is methoxy, 2,2,2-trifluoroethoxy or methoxypropoxy, R40 is hydrogen or methyl and wherein all hydrogen atoms of R30 are replaced by deuterium atoms.

14. A compound of formula 10 according to claim 1, wherein R30 is methoxy, 2,2,2-trifluoroethoxy or methoxypropoxy and wherein all hydrogen atoms of R30 are replaced by deuterium atoms.

15. A compound of formula 10 according to claim 1, wherein R10 is hydrogen, methoxy or difluoromethoxy, R20 is methyl or methoxy, R30 is methoxy, 2,2,2-trifluoroethoxy or methoxypropoxy, R40 is hydrogen or methyl and wherein all hydrogen atoms of R30 are replaced by deuterium atoms.

16. A compound of formula 10 according to claim 1, wherein R10 is methoxy, R20 is methyl, R30 is methoxy, R40 is methyl or wherein R10 is hydrogen, R20 is methyl, R30 is 2,2,2-trifluoroethoxy or methoxypropoxy, R40 is hydrogen or wherein R10 is difluoromethoxy, R20 is methoxy, R30 is methoxy, R40 is hydrogen and wherein all hydrogen atoms of R30 are replaced by deuterium atoms.

17. A compound of formula 10 according to claim 1, selected from the group consisting of 5-methoxy-2-((4-trideuteriomethoxy-3,5-dimethyl-2-pyridylmethyl)sulphinyl)-1H-imidazo[4,5-b]pyridine, 5-trideuteriomethoxy-2-((4-trideuteriomethoxy-3,5-dimethyl-2-pyridylmethyl)sulphinyl)-1H-imidazo[4,5-b]pyridine, 5-methoxy-2-((3-methyl-4-trideuteriomethoxy-5-trideuteriomethyl-2-pyridylmethyl)sulphinyl)-1H-imidazo[4,5-b]pyridine, 5-trideuteriomethoxy-2-((3-methyl-4-trideuteriomethoxy-5-trideuteriomethyl-2-pyridylmethyl)sulphinyl)-1H-imidazo[4,5-b]pyridine and the salts and enantiomers thereof.

18. The compound of formula 10 according to claim 1, (R/S)-5-methoxy-2-((4-trideuteriomethoxy-3,5-dimethyl-2-pyridylmethyl)sulphinyl)-1H-imidazo[4,5-b]pyridine, and pharmaceutically acceptable salts thereof.

19. A compound of formula 20

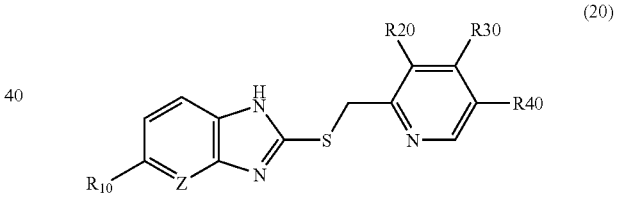

(20)

in which
R10 is hydrogen, difluoromethoxy or 1-4C-alkoxy,
R20 is 1-4C-alkyl or 1-4C-alkoxy,
R30 is 1-4C-alkyl, 1-4C-alkoxy 2,2,2-trifluoroethoxy or 2-8C-alkoxyalkoxy,
R40 is hydrogen or 1-4C-alkyl,
Z is N,
or a salt or enantiomer thereof,
wherein at least one of hydrogen atom of R10, R20, R30, R40 or any combination of R10, R20, R30 and R40 is replaced by a deuterium atom.

20. A pharmaceutical composition comprising a compound of formula 10 according to claim 1 or a pharmaceutically acceptable salt or enantiomer thereof, together with one or more pharmaceutically acceptable excipients.

21. The pharmaceutical composition according to claim 20, wherein a single dose comprises from about 2 to about 60 mg of the compound of formula 10.

* * * * *